United States Patent [19]

Albarella et al.

[11] Patent Number: 5,210,217

[45] Date of Patent: May 11, 1993

[54] SUBSTITUTED BITHIOPHENES AND DITHIENYLPYRROLES

[75] Inventors: James P. Albarella, Elkhart; J. Oakey Noell; Paul O. Vogelhut, both of Mishawaka; Frederick E. Ward, deceased, late of Elkhart, all of Ind., by Linda Ward, administrix

[73] Assignee: Miles Inc., Elkhart, Ind.

[21] Appl. No.: 335,563

[22] Filed: Apr. 10, 1989

Related U.S. Application Data

[62] Division of Ser. No. 114,011, Oct. 29, 1987, Pat. No. 4,886,625.

[51] Int. Cl.$^5$ .................. C07D 409/04; C07D 409/14
[52] U.S. Cl. ........................ 548/527; 549/59; 549/90; 252/500; 548/314.7; 548/465
[58] Field of Search ................ 252/500; 548/518, 527, 548/465; 549/59, 60, 472, 473, 74, 76, 77, 90

[56] References Cited

U.S. PATENT DOCUMENTS

| | | | |
|---|---|---|---|
| 4,691,005 | 9/1987 | Sato et al. | 252/500 |
| 4,711,742 | 12/1987 | Jen et al. | 252/518 |
| 4,711,946 | 12/1987 | Jenekhe et al. | 252/500 |
| 4,731,311 | 3/1988 | Suzuki et al. | 252/500 |
| 4,795,687 | 1/1989 | Suzuki et al. | 252/500 |
| 4,886,625 | 12/1989 | Albarella et al. | 252/500 |
| 5,068,355 | 11/1991 | Albarella et al. | 548/527 |

FOREIGN PATENT DOCUMENTS 62-226567 10/1987 Japan .

*Primary Examiner*—Paul Lieberman
*Assistant Examiner*—Bradley A. Swope
*Attorney, Agent, or Firm*—Jerome L. Jeffers

[57] ABSTRACT

Electrically conducting homo- and/or copolymers and/or tripolymers can be produced from novel monomers, such as a 3-substituted 2,5-di(2-thienyl)pyrrole. The polymers exhibit unexpectedly high stability and conductivities, and can be functionalized, such as with an enzyme, like glucose oxidase, or an ion-specific binding site, like a crown ether, or an antigen, without adversely affecting the conductivity of the polymer. The functionalized, conducting polymer can be used in a diagnostic device to determine the presence and concentration of a specific analyte in a liquid medium. For example, the presence and concentration of glucose is determined by measuring the conductivity change in the polymer caused by the vibrational excitation induced in the enzyme, glucose oxidase, from its reaction with the glucose and/or by measuring a secondary effect of the enzyme/substrate reaction, such as the change in the conductivity of the conducting polymer caused by the generation of hydrogen peroxide during the glucose-glucose oxidase reaction.

3 Claims, No Drawings

SUBSTITUTED BITHIOPHENES AND DITHIENYLPYRROLES

This is a division of application Ser. No. 114,011, filed Oct. 29, 1987, now U.S. Pat. No. 4,886,625.

FIELD OF THE INVENTION

The present invention relates to a method of determining analyte concentrations by utilizing analyte sensors that employ conducting organic polymers. More particularly, conducting polymers, synthesized from novel monomers, can be covalently functionalized with an enzyme, antigen or an ion specific binding site, and employed in a diagnostic device to selectively assay a liquid medium for the presence and concentration of a specific analyte. The presence and concentration of the specific analyte is determined by measuring the change in conductivity of the polymer arising either from transduction of the vibrational excitation induced in the covalently-bound functionality by the reaction of the functionality with the analyte, and/or by measuring the change in conductivity of the polymer arising from secondary effects of the reaction between the covalently-bound functionality and the analyte, such as the generation of hydrogen peroxide. Surprisingly and unexpectedly, the monomers utilized to prepare the organic conducting polymers of the present invention yield polymers having a high degree of stability and conductivity. The monomers, each having a five-membered heteroaromatic ring substituted in the three position, provide polymers having unexpectedly high conductivities compared to prior art conducting polymers prepared from functionalized five membered heteroaromatic ring compounds. Even more surprisingly, this high degree of polymer conductivity is maintained after functionalization of the polymer with an enzyme, antigen or ion-specific binding site. As a result, functionalized conducting polymers are available for use in diagnostic devices to determine analyte concentrations in liquid media.

BACKGROUND OF THE INVENTION

Investigators have shown an intense interest in organic conducting polymers that can be synthesized chemically, like polyacetylene, or electrochemically, like polypyrrole and polythiophene. The organic conducting polymers have several potential applications in the fields of batteries, display devices, corrosion prevention in metals and semiconductors and in microelectronic devices such as diodes, transistors, sensors, light emitting devices and energy conversion and storage elements. However, present day organic conducting polymers possess several limitations that have hindered the expansion of organic conducting polymers into these and other potential application areas. The limitations found in the three most extensively studied conducting polymers, polyacetylene, polypyrrole and polythiophene, illustrate the general problems encountered by investigators in the field of conducting polymers and why the use of conducting polymers has been impeded.

For example, polyacetylene, among the first organic conducting polymers, is prepared chemically from acetylene by using an appropriate catalyst. As prepared chemically, polyacetylene is an insulator, exhibiting conductivities in the range of $10^{-10}$ S/cm to $10^{-13}$ S/cm (Siemens per centimeter) that correspond to the conductivity of known insulators, such as glass and DNA. However, polyacetylene can be doped using a variety of oxidizing or reducing agents, such as antimony pentafluoride, the halogens, astatine pentafluoride, or aluminum chloride. By doping, polyacetylene is converted into a highly conducting polymer, exhibiting a conductivity of approximately $10^3$ S/cm, therefore exhibiting the conductivity of metals such as bismuth. However, polyacetylene suffers from the drawbacks of extreme instability in air and a precipitous drop in conductivity whenever an acetylenic hydrogen is replaced by an alkyl or other substituent group. Accordingly, the instability of polyacetylene in the presence of oxygen, and its inability to be functionalized and maintain its high conductivity, makes the polyacetylenes unsuitable conducting polymers for use as an analyte sensor.

Polypyrrole, a conducting polymer similar to polyacetylene, can be synthesized chemically or electrochemically and exhibits conductivities ranging from about 1 S/cm to about 100 S/cm. As will be discussed more fully hereinafter, conducting polypyrrole is a doped material, incorporating the anion of the supporting electrolyte. Polypyrrole having a molecular weight of up to approximately 40,000 has been synthesized; however, conductivity is observed in polypyrrole containing as few as six monomer units. Normally, polypyrrole, and other conducting polymers, are low molecular weight polymers containing less than 100 monomer units.

Investigators have found that placing alkyl groups on either the nitrogen or the carbons of the heteroaromatic pyrrole ring decreases the conductivity of polypyrrole. For example, an unsubstituted polypyrrole, incorporating the tetrafluoroborate anion as the compensating counterion, exhibits a conductivity of 40 S/cm, whereas the N-methyl derivative, incorporating the same dopant, exhibits a conductivity of $10^{-3}$ S/cm; the three-methyl derivative of pyrrole exhibits a conductivity of 4 S/cm; 3,4-dimethyl derivative, a conductivity of 10 S/cm; and the 3,4-diphenyl derivative, a conductivity of $10^{-3}$ S/cm.

The conductivity decrease in substituted polypyrroles is attributed to several factors. First, and of prime importance, the substituent introduced onto the heteroaromatic pyrrole ring cannot alter the oxidation potential of the parent heteroaromatic to the extent that electropolymerization at the anode is precluded. Secondly, and a related consideration, the aromatic pi-electron system of the parent heterocycle must be maintained. Disruption of the pi-electron system of the heteroaromatic ring will adversely affect the relative stability of the aromatic and quinoid-like forms, illustrated as structures I and II, respectively, and therefore seriously reduce conductivity. A third critical consideration is that the functionality introduced onto the parent heterocycle must not create steric demands that preclude the adoption of a planar configuration by the conducting polymer.

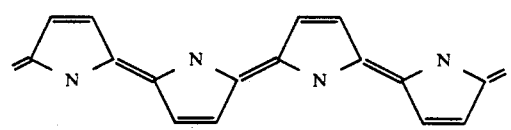

I

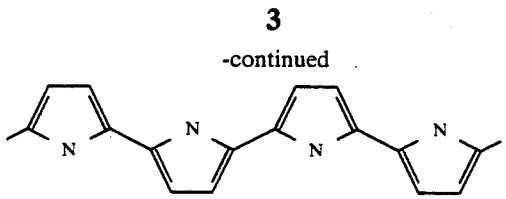

II

The requirement that the conducting polymer must maintain a planar configuration has seriously hindered development of functionalized, conducting polymers. Numerous N-alkyl and N-aryl derivatives of polypyrrole have been prepared and discussed in the literature. However, it was found that even the simplest of these N-substituted polypyrroles, poly-N-methylpyrrole, exhibits conductivities that are three orders of magnitude lower than unsubstituted polypyrrole films doped with the same counterion. It is also possible to produce thin films of poly-N-aryl pyrroles, wherein the phenyl group is further substituted in the para position. However, polymers produced from these N-aryl pyrroles invariably exhibit conductivities three or more orders of magnitude less than the parent unsubstituted pyrrole. Such low conductivities preclude the use of these substituted polypyrroles in the development of analyte sensors.

The steric interactions introduced by the pyrrole ring substituents is important because of the mechanism of charge transport through the conducting polymer system. In one charge transport mechanism, electric charge is conducted through the polymer chain itself because of bipolaron structures that exist along the polymer chain. The bipolaron structure, illustrated in structure III and confirmed from spectroscopic evidence obtained on polythiophene, are defects occurring in the polymer lattice wherein two dopant counterions, $A^-$, from the supporting electrolyte, balance two positive centers found in the polymer.

It also should be noted that investigators have found that R and/or R' substituents in structure IV should not be strongly electron-withdrawing or strongly electron-donating, as strong electronic effects also can serve to destroy the conductivity of the polymer. However, it has been found, especially for N-substituted pyrroles, that steric interactions, not electronic effects, are the main factor in determining polymerizability, polymer conductivity, and cyclic stability of the polymer between the doped and undoped state. Steric interactions in polythiophene derivatives are somewhat less dominant than those observed in polypyrrole derivatives. Steric interactions in polypyrrole derivatives are more dominant because the predominant destabilizing interactions in pyrrole derivatives involve the hydrogen atom of the pyrrole nitrogen. These steric interactions are avoided in polythiophenes. As a result, electronic effects play a more central role in polythiophene derivatives.

Conducting organic polymers generally are amorphous, disordered materials, and as a result, if bulk conductivity is to be sustained, charge transport must occur between polymer strands as well as along single polymer strands. The probability of the interchain charge transport is directly related to the distance between chains. The distance between polymer chains is acutely sensitive to, and dependent upon, two factors, the nature and size of the dopant counterion and the character and steric requirements of the R and R' substituents of structure IV. This steric requirement imposes a significant constraint on the design of functionalized conducting polymers.

The synthesis and conductivities of polypyrrole and substituted polypyrroles have been extensively investigated as seen in the general references cited below. These references include the information discussed

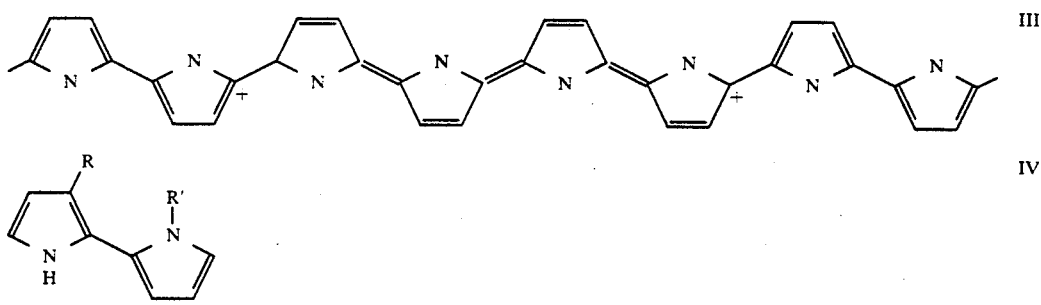

III

IV

Generally, the two positive centers are spaced, and confined, by approximately four monomer units and these defects serve to transport charge along the polymer chain. However, in order to transport charge along the chain, compositions having the structures I, II and/or III must be planar, such that the charge can be transported along the planar pi-electron system of the chain. As can be seen in structure IV, if the substituents R and/or R' are sufficiently large, the steric interaction between R and R' can distort the pyrrole monomer units out of planarity, therefore destroying the planarity of the pi-electron system, and destroying, or seriously reducing, the conductivity of the polymer. As illustrated by the large conductivity drop in polypyrroles having substituents positioned on the pyrrole ring, even substituents as small as a methyl group introduce steric interactions sufficient to essentially destroy the conductivity of the polymer.

above and general information concerning the polypyrroles, such as that the specific dopant ($A^-$) in structure III can seriously affect the conductivity of the polymer; that conductivity is observed only for alpha-alpha coupling of monomers and not for alpha-beta coupling of monomers (see structure V); and that polypyrrole films are stable, insoluble, and inert to most reagents, except possibly treatment by alkalis. The conductivity and stability of polypyrrole makes polypyrrole a good candidate for use in analyte sensors, if the polypyrrole conductivity can be maintained when functional groups are introduced onto the heteroaromatic ring.

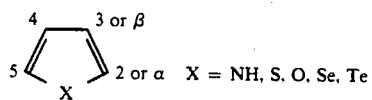

V

The representative references discussing the polypyrroles include:

G. Bidan, Tet. Lett. 26(6), 735–6 (1985).

P. Audebert, G. Bidan, an M. Lapowski, J. C. S. Chem. Comm., 887 (1986).

M. S. Wrighton, Science 231, 32 (1986).

R. A. Simon, A. I. Ricco and M. S. Wrighton, J. Am. Chem. Soc, 104, 2034 (1982).

A. F. Diaz, J. Castillo, K. K. Kanazawa, J. A. Logan, M. Salmon and O. Fojards, J. Electroanal. Chem. 133, 233 (1982).

M. Saloma, M. Aguilar and M. Salmon, J. Electrochem. Soc. 132, 2379 (1985).

M. V. Rosenthal, T. A. Skotheim, A. Melo, M. I. Florit, and M. Salmon, J. Electroanal. Chem. and Interfac. Chem. 1, 297 (1985).

G. Bidan and M. Guglielmi, Synth. Met. 15, 51 (1986).

M. Salmon and G. Bidan, J. Electrochem. Soc., 1897 (1985).

E. M. Genies and A. A. Syed, Synth. Met. 10, 27 (1984/85).

G. Bidan, A. Deronzier and J. C. Moutet, Nouveau Jour. de Chimie 8, 501 (1984).

J. P. Travers, P. Audebert and G. Bidan, Mol. Cryst. Liq. Cryst. 118, 149 (1985).

Another well-studied conducting polymer is polythiophene, wherein thiophene (structure V, X=S) is electrochemically polymerized to yield a stable conducting polymer. Similarly, furan (structure V, X=O) also yields a stable conducting polymer similar to polypyrrole and polythiophene. Polythiophene resembles polypyrrole in that polythiophene can be cyclized between its conducting (oxidized) state and its nonconducting (neutral) state without significant chemical decomposition of the polymer and without appreciable degradation of the physical properties of the polymer. Polythiophene, like polypyrrole, exhibits conductivity changes in response both to the amount of dopant and to the specific dopant, such as perchlorate, tetrafluoroborate, hexafluorophosphate, hydrogen sulfate, hexafluoroarsenate and trifluoromethylsulfonate.

Substituents placed on the heteroaromatic thiophene ring can affect the resulting conducting polymer. For example, thiophene polymerization can be affected by large substituents at the 3 and 4 positions, as seen in the inability of 3,4-dibromothiophene to polymerize. The electronic and steric effects introduced by the 3,4-dibromo substituents may prevent chain propagation. However, in contrast to pyrrole, ring substituents on thiophene do not seriously reduce the conductivity of the resulting heteroaromatic polymer. For example, it has been found that for 3-methylthiophene and 3,4-dimethylthiophene, the resulting substituted polythiophene exhibited an improved conductivity compared to the parent polythiophene, presumably due to enhanced order in the polymer chain of the substituted thiophene. However, the methyl group is not a suitable substituent for the subsequent polymer surface functionalization needed to produce an analyte sensor.

The following are representative references concerning the synthesis and conductivity of polythiophene and substituted polythiophenes:

G. Tourillon, "Handbook of Conducting Polymers," T. A. Skotheim, ed., Marcel Dekker, Inc., New York, 1986, p. 293.

R. J. Waltham, J. Bargon and A. F. Diaz, J. Phys. Chem. 87, 1459 (1983).

G. Tourillon and F. Garnier, J. Polym. Sci. Polym. Phys. Ed. 22, 33 (1984).

G. Tourillon and F. Garnier, J. Electroanal. Chem. 161, 51 (1984).

A. F. Diaz and J. Bargon, "Handbook of Conducting Polymers," T. A. Skotheim, ed., Marcel Dekker, Inc., New York 1986, p. 81.

J. Bargon, S. Mohmand and R. J. Waltman, IBM, J. Res. Dev. 27, 330 (1983).

G. Tourillon and F. Garnier, J. Phys. Chem. 87, 2289 (1983).

A. Czerwinski, H. Zimmer, C. H. Pham, and H. B. Mark, Jr., J. Electrochem. Soc. 132, 2669 (1985).

From the studies on the polyacetylenes, polypyrroles and polythiophenes, and from related studies on other conducting polymers, including polyparaphenylene, polyazulene, polycarbazole, polypyrene, polyaniline and polytriphenylene, it is apparent that a delicate balance exists between the electronic effects and the steric effects introduced by the substituents that renders a polymer of a substituted five or six member heteroaromatic ring more conducting or less conducting than the unsubstituted parent heteroaromatic compound. Therefore, it would be advantageous to develop a monomer that can be readily polymerized, chemically or electrochemically, to yield a conducting polymer having sufficient conductivity such that the polymer can be used as an analyte sensor in a diagnostic device to determine the presence and concentration of an analyte in liquid media.

It is also apparent that a functionalized conducting polymer is required for ultimate use as an analyte sensor. The polymer must not only possess sufficient conductivity, but the polymer also must contain moieties that can interact with the analyte of interest. This interaction then must sufficiently alter the conductivity of the polymer in order to measurably detect the conductivity difference and convert this conductivity change into an analyte concentration. It is to such a conducting polymer that the method of the present invention is directed.

The prior art does not include any known references to the method of the present invention. The prior art chemical modifications to conducting polymers were unconcerned with the retention of high conductivity. For example, M. S. Wrighton et al, in the references cited above, have developed N-alkylpyrroles in an attempt to improve the binding of a polymer film to a platinum electrode. In this study, only a very thin layer of functionalized polypyrrole in contact with the electrode is required, therefore making the conductivity of the essentially monolayer film unimportant.

Saloma et al (J. Electrochem. Soc. 32, 2379 (1985)) have attempted to functionalize polymer films in order to modify electrode properties. Saloma et al attempted to utilize the conductivity of the functionalized polymer as an electronic mediator for any chemical effects occurring on the attached moiety. However, this particular research area has been bypassed by similar chemical modifications of metal electrodes (R. W. Murray, Acc. Chem. Res. 13, 135 (1980)).

M. V. Rosenthal et al disclosed, in M. V. Rosenthal, T. A. Skotheim, C. Linkous and M. I. Florit, Polym. Preprints 25, 258 (1984) and in M. V. Rosenthal, T. A. Skotheim, J. Chem. Soc. Chem. Commun 6, 342 (1985), an attempt to derivatize polypyrrole after polymerization.

The above referenced prior art concerning substituted pyrrole and substituted thiophene polymers is not directed to preparing conducting polymers for use as an analyte sensor in a diagnostic device. For example, films prepared from the methyl derivative of thiophene were not synthesized in order to attempt subsequent polymer surface functionalization, but rather to prevent monomeric couplings through the beta positions in order to introduce greater order, and therefore greater conductivity, into the polymer. In the referenced prior art, the investigators attempted to characterize and improve polymer properties, as opposed to chemically utilizing the substituents on the heteroaromatic ring.

During the course of the investigations on the synthesis and polymerization of functionalized 2,5-dithienylpyrrole derivatives, the electrochemical polymerization and the properties of the parent molecule, poly[2,5-di(2-thienyl)pyrrole], was disclosed by G. G. McLeod, M. G. B. Mahoubian-Jones, R. A. Pethuck, S. D. Watson, N. D. Truong, J. C. Galiri, and J. Francois in Polymer 27 (3), 455-8 (1986). The molecule, 2,5-di(2-thienyl)pyrrole (structure VI), is the parent heteroaromatic monomer that forms the basis of the method of the present invention. Although the primary objective o McLeod et al was to determine the solubility of the polymer resulting from 2,5-di(2-thienyl)pyrrole (VI), the polymerization of 2,5-di(2-thienyl)pyrrole was interesting for several additional reasons. For example, poly[2,5-di(2-thienyl)pyrrole] is readily synthesized electrochemically and, when anion doped, exhibits an electric conductivity analogous to polypyrrole and polythiophene.

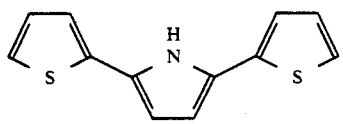

VI

However, most surprisingly and unexpectedly, and in accordance with the method of the present invention, 2,5-di(2-thienyl)pyrrole can be functionalized at the three-position of the pyrrole ring, and yield conducting polymers that exhibit the high conductivity of the unsubstituted parent dithienylpyrrole (VI). As will be discussed in the detailed description of the invention, a variety of functional groups can be incorporated into the three-position of the pyrrole ring of 2,5-di(2-thienyl)pyrrole without adversely affecting the conductivity of the resulting polymer.

In addition to the novel monomers used to synthesize the conducting polymers of the present invention, the conducting polymers can be further derivatized, after polymerization, to allow the detection and measurement of a specific analyte. According to the method of the present invention, postpolymerization derivatization and functionalization of the conducting polymer permits detection and measurement of a specific analyte by coupling the vibrational energy resulting from the functionalized polymer-analyte reaction to the phonon modes of the polymer. As used here, and throughout the specification, a phonon is a quantized, delocalized vibrational or elastic state of the polymer lattice.

Although several references disclose the use of conducting organic polymers in sensors, no known prior art references utilize the vibrational energy coupling of the analyte reaction to the conducting polymer. In fact, none of the present conducting polymer-based sensors involve an analyte probe molecule covalently bound to, and acting in concert with, the polymer. In contrast, the prior art sensors are based upon a direct interaction of an analyte, usually a gas, with the polymer. It should be noted however that the conducting polymers used in the present invention also can be used as an analyte sensor by direct interaction with the analyte.

The most common mode of direct interaction between the analyte and the conducting polymer is to affect the state of oxidation of the organic conducting polymer. As will be discussed more fully in the detailed description of the invention, the existence of bipolaron, and therefore the conductivity of the polymer, depends upon having the polymer oxidized, with the oxidation state supported by dopant counterions. Sensors then can be developed based upon either compensating conducting films or chemically-doping reduced films.

For example, M. S. Wrighton et al, in European Patent No. 185,941, discloses the use of conducting organic polymers as the active species in a chemical sensor. The patent generally teaches using the changes in physical properties of the conducting polymer as the active transduction into electrical signals. Specific examples cited in the patent include detection of oxygen gas, hydrogen gas, pH and enzyme substrate concentrations. The Wrighton et al patent neither teaches the coupling of an analyte/probe molecule vibrational interactions to the vibrational manifold of the polymer nor teaches the use of such vibrational coupling as a transduction mechanism for analyte detection. In contrast, the principal transduction mechanism described by Wrighton et al is the direct use of the change in polymer conductivity induced by oxidation or by reduction.

An additional mode of substrate/polymer interaction that is suitable for sensor development has been described in the prior art. It has been shown that it is possible to utilize the change of the surface dielectric attending the absorption of an analyte upon a polypyrrole film to make an alcohol sensor. In addition to novel electronic transduction mechanisms, the prior art also describes the use of a suspended gate, field effect transistor. Such electronic structures are in most ways analogous to well known structures employing inorganic semiconductors, and they can be expected to be generically useful in sensor development. In the embodiment of the invention described herein, a chemiresistor device configuration is used. It is anticipated, however, that evolutionary improvements will utilize the gated structures as described in the prior art.

The following references are representative of the state of the art of electrochemical sensors using heteroaromatic polymers:

Y. Ikariyama and W. R. Heineman, Anal. Chem. 58, 1803 (1986).

M. Josowicz and J. Janata, Anal. Chem. 58, 514 (1986).

T. N. Misra, B. Rosenberg and R. Switzer, J. Chem. Phys. 48, 2096 (1968).

K. Yoshino, H. S. Nalwa, J. G. Rabe and W. F. Schmidt, Polymer Comm. 26, 103 (1985).

C. Nylander, M. Armgrath and I. Lundstrom, Anal. Chem. Symp. Ser. 17 (Chem Sens) 159 (1983).

H. S. White, G. P. Kittlesen and M. S. Wrighton, J. Am. Chem. Soc. 106, 5317 (1984).

G. P. Kittlesen, H. S. White and M. S. Wrighton, J. Am. Chem. Soc. 106, 7389 (1984).

Malmros, U.S. Pat. No. 4,444,892, disclosing a device having an analyte specific binding substance immobilized onto a semiconductive polymer to allow detection of a specific analyte.

European Patent No. 193,154, filed Feb. 24, 1986, disclosing immunosensors comprising a polypyrrole or polythiophene film containing an occluded antigen or antibody.

M. Umana and J. Waller, Anal. Chem. 58, 2979 (1986) disclosed the occlusion, or trapping, of an enzyme, glucose oxidase, by electropolymerizing pyrrole in the presence of the enzyme. The polypyrrole containing the occluded enzyme then can be used to detect glucose. The method of the present invention however differs significantly in that according to the present invention the enzyme is covalently bound to the conducting polymer after polymerization.

The following references are cited to further show the state of the prior art and to serve as additional background material for the method of the present invention:

Vibrational energy transport in proteins:
- A. S. Davydov, J. Theor. Biol. 38, 559 (1973).
- A. S. Davydov, Physica. Scripta. 20, 387 (1979).
- A. S. Davydov, studia biophysica (Berlin) 62, 1 (1977).
- A. C. Scott, "Nonlinear Electrodynamics in Biological Systems," M. Ross Adey and A. L. Lawrence, eds., Plenum Press, NY, 1984, p. 133.
- C. F. McClare, Nature 296, 88 (1972).

A preferred synthesis of the parent molecule 2,5-di(2-thienyl)pyrrole:
- H. Weinberg and J. Metselur, Syn, Comm. 14(1), 1 (1984).

The preparation of pyrrole derivatives by 1,3-dipolar cycloaddition:
(1) R. Huisgen, H. Gotthardt and H. O. Bayer, Chem. Ber. 103, 2368 (1970).
(2) J. W. Lown and B. E. Landberg, Can. J. Chem. 52, 798 (1974).

SUMMARY OF THE INVENTION

In brief, the present invention is directed to analyte sensors utilizing conducting organic polymers. More particularly, the present invention is directed to a novel class of monomers that yield conducting polymers having substituent groups capable of functionalization. The conducting polymers can undergo postpolymerization reactions to bond covalently to an analyte-specific probe molecule onto the polymer surface for detection of a specific analyte and measurement of the analyte concentration. Additionally, the conducting polymers produced according to the method of the present invention allow the detection and measurement of a specific analyte in liquid media through a new transduction mechanism not previously observed in conducting polymers.

The analyte sensors used according to the method of the present invention utilize the unique electrical conducting properties of heteroaromatic polymers to determine the presence and concentration of a specific analyte. According to the method of the present invention, the analyte sensors use a conducting polymer having an analyte-specific probe molecule covalently bound to the polymer surface. The conductivity of the polymer is altered by the interaction between the probe molecule and the analyte, and the measurable effect is detected through either a direct coupling of the vibrational interactions between the analyte-probe molecule with the conducting polymer or through secondary effects produced by reaction products. If the interaction between the analyte, probe molecule and the conducting polymer is detected through a direct linkage of the vibrational energy of the probe-analyte interaction to the phonon-assisted bipolaron transport of the polymer, then the probe molecule must be covalently bonded to the polymer surface to insure vibrational coupling. Additionally, if the electrical detection mechanism involves the chemical effect of a secondary reaction species, such as enzyme-substrate generated hydrogen peroxide, upon the polymer, then direct covalent bonding between the probe molecule and the polymer enhances detection efficiency by providing a high surface concentration of the secondary reaction product.

Examples of probe molecules that can be covalently bound to the conducting polymer surface include enzymes, antigens, and ion specific binding sites, such as crown ethers. The analyte detection mechanism in the conducting polymer includes direct observation of molecular vibrations resulting from enzyme/substrate or antigen/antibody reactions. As a particular example, the vibrational excitation induced in a protein by an enzyme/substrate reaction can be transported through the protein in a localized waveform termed a soliton. The localized energy of the soliton then could be transmitted to the phonon modes of the conducting polymer by properly selecting the length and stiffness of the molecular arm covalently bridging the probe molecule and the polymer. The conductivity of the polymer is therefore directly modulated because of the dependence of the electrical properties of doped heteroaromatic polymers upon the excitations of the internal vibrational states caused by the enzyme/substrate reaction.

The transducing of the probe/analyte vibrational interaction into an electrical signal within the polymer can be assisted by a secondary process. For example, the detection of the reaction product of an enzyme/substrate reaction, either through direct compensation of the dopant counterion, or, more reversibly, through the use of a counterion as a catalyst within the polymer. A specific example of this latter mechanism is the use of tetrachlororuthenate ($RuCl_4^-$) or tetrachloroferrate (III) ($FeCl_4^-$) ions as a dopant-catalyst for the oxidation of hydrogen peroxide. As an example, hydrogen peroxide is generated in the reaction of glucose oxidase with glucose in the presence of oxygen. Therefore, by measuring the concentration of hydrogen peroxide, the concentration of glucose in solution can be indirectly determined. The use of a dopant catalyst as an electrical transducer in heteroaromatic polymers is disclosed in U.S. Pat. No. 4,560,534 to Kung et al, and hereby incorporated by reference.

The Kung et al patent teaches using a conducting polymer, polypyrrole, doped with an anionic counterion-catalyst containing iron, ruthenium or other group VIII metals as a catalyst for hydrogen peroxide decomposition. However, according to the method of the present invention, the ability to covalently couple a probe molecule to the conducting polymer surface is a significant improvement because the covalent bond effectively enhances the transducing mechanism by insuring a high local surface concentration of the hydrogen peroxide.

In accordance with the present invention, a new class of conducting organic polymers that are functionalized with chemically-reactive substituents and that maintain sufficient conductivity for use in electrical sensors were developed. It also has been demonstrated that probe molecules can be covalently attached to the surface of the conducting polymer without seriously reducing the conductivity of the polymer film. In particular, it has been demonstrated that glucose oxidase can be covalently attached to a conducting polymer film. Moreover, it has been shown that by utilizing a covalent attachment of the probe molecule to the polymer surface, it is possible to design and construct a diagnostic device that exhibits a hydrogen peroxide dose response utilizing catalytic transduction.

In addition, it also has been demonstrated that the covalent bonding of an enzyme to a conducting polymer has enabled a direct electrical transduction of the glucose oxidase/glucose reaction. A significant factor in the detection of glucose has been the effect of the generated hydrogen peroxide upon the conductivity of the polymer. However, evidence exists for the operation of a direct vibrational coupling mechanism between the enzyme/substrate reaction and the conducting polymer. In accordance with an important feature of the present invention, the direct vibrational coupling mechanism can occur because of the ability to covalently attach an enzyme, antigen or receptor molecule to the conducting polymer surface.

According to the method of the present invention, a novel class of polymers, demonstrating a high degree of conductivity and the capability of subsequent polymer surface functionalization, is generally based upon the monomer, 2,5-di(2-thienyl)pyrrole (structure VI). Although the electropolymerization of monomer (VI) has been reported, the prior art does not contain any known references pertaining to the monomers utilized to synthesize the conducting polymers of the present invention. More particularly, the conducting polymers of the present invention are synthesized from monomers having a reactive functionality incorporated at the three position of the pyrrole ring as shown generally in structure VII.

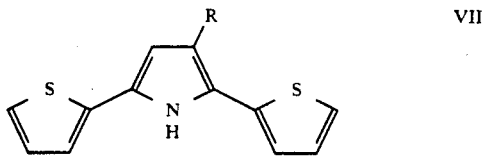
VII

The novel feature of the monomers having the general structure VII enabling the growth of highly conducting polymers, despite the presence of a substituent at the three-position of the pyrrole ring, is that the central pyrrole ring is flanked by two thiophene rings. The resulting steric interaction between the three-position substituent (R) with the 2-and 5-position thiophene rings is decreased significantly in comparison to the corresponding terpyrrole structure that has a hydrogen atom in proximity to the three-position substituent. Thus, the three-position substituted 2,5-di(2-thienyl)pyrrole VII can assume a more planar structure, and upon polymerization yield a film having a higher conductivity, than its terpyrrole analog.

Analogously, and because oxidation potentials drop as oligomer size increases, the following classes of molecules, depicted generally by structures VIII, IX and X, also can serve as suitable monomers for the synthesis of functionalized conducting polymers. Similarly, substituted furan monomers also can yield conducting polymers, however, the conductivity of these substituted polyfurans will be quite low due to the decreased aromaticity of the parent rings.

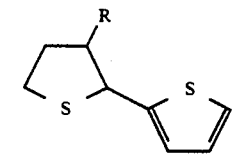
VIII

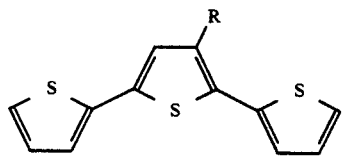
IX

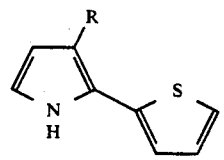
X

Various members of the substituted 2,5-di(2-thienyl)pyrrole monomers having general structure VII have been synthesized, then polymerized electrochemically. As will be discussed more fully hereinafter, the 2,5-di(2-thienyl)pyrrole monomers of structure VII yield stable polymer films having conductivities significantly greater than the conductivities exhibited by the derivatized conducting polymer films of the prior art. It also has been found that the 2,5-di(2-thienyl)pyrrole monomers of structure VII can be copolymerized with pyrrole, or other like unsubstituted parent heteroaromatics, to yield stable conducting polymer films.

Surprisingly, in addition to synthesizing stable conducting polymers from the three-position substituted 2,5-di(2-thienyl)pyrrole monomers (VII), it also has been found that postpolymerization chemistry can be performed on the three-position substituents of the pyrrole ring. Such postpolymerization reactions are most surprising and unexpected because the steric availability and the chemical environment of the three-position substituent is modified by polymerization.

The first demonstration of polymer surface reactivity was the reaction of poly(3-acetyl-2,5-dithienylpyrrole) and phenylhydrazine to yield the corresponding hydrazone derivative. However, this particular reaction was difficult to monitor because the phenylhydrazine reduced the counterion dopant, and therefore reduced the conductivity of the resulting film. Another, more useful demonstration of polymer surface reactivity, to be discussed more fully hereinafter, was the conversion of the copolymer of 3-N-trifluoroacetamidomethyl-2,5-di(2-thienyl)pyrrole (XIX) and pyrrole to the 3-aminomethyl-2,5-dithienylpyrrole copolymer by removing the trifluoroacetyl group. Then, through any one of a variety of available reactions, glucose oxidase was covalently attached to the free amine moiety present on the copolymer surface.

The covalently-bound probe molecule, such as glucose oxidase, now provides an analyte sensor utilizing a new sensing mechanism to directly determine the presence and amount of an analyte, such as glucose, in a liquid medium. Furthermore, the covalent bonding of the probe molecule to the conducting polymer offers the major advantage of monitoring the formation or decomposition of secondary reaction products, such as hydrogen peroxide. A protein probe molecule covalently bound to the conducting polymer surface allows the direct transfer of the enzyme/substrate or antigen-/antibody reaction vibrational energy, possibly via soliton transport, into the phonon modes of polymer, thereby directly affecting polymer conductivity. This direct transduction of the enzyme/substrate or antigen-/antibody reaction is not possible using existing detection techniques. In fact, antigen/antibody reactions have proved to be particularly difficult to monitor electrically because of a lack of attendant charge transfer in the reaction.

The covalent binding of probe molecules to conducting polymer surfaces also offers advantages in regard to secondary detection mechanisms by affording an intimate contact between the source and the detector. For example, if glucose oxidase is covalently bound to the surface of the conducting polymer, the generation of hydrogen peroxide during the enzyme reaction with glucose occurs at the polymer surface. This results in a higher local concentration of hydrogen peroxide at the conducting polymer surface and therefore a more efficient transduction, and sensing, mechanism. Overall, the advantages for secondary detection mechanisms that are realized by covalently binding enzymes to the conducting polymer are analogous to the advantages offered by the similar covalent binding of enzymes to the active electrode in amperometric, electrochemical detectors.

Therefore, it is an object of the present invention to provide a method of determining analyte concentrations in liquid media by utilizing organic conducting polymers. It is also an object of the present invention to provide a method for determining analyte concentrations in liquid media wherein the analyte interacts with a probe molecule that is covalently attached to the conducting polymer.

Another object of the present invention is to provide a method of determining analyte con- centrations through the interaction of an analyte with a probe molecule such that a detectable and measurable conductivity change occurs in the conducting polymer and establishes the presence and concentration of the analyte.

Another object of the present invention is to provide a method of determining analyte concentrations in liquid media from a conductivity change in the conducting polymer caused by the reaction between the covalently attached probe molecule and the analyte, and detected by transferring the vibrational energy from the probe molecule-analyte reaction to the conducting polymer, and the transduction of that vibrational energy into an electrical signal.

Another object of the present invention is to provide a method of determining analyte concentrations in liquid media wherein the conductivity change in the conducting polymer, caused by the reaction between the probe molecule and the analyte, results from secondary processes of the probe molecule-analyte reaction, such as the generation and detection of hydrogen peroxide.

Another object of the present invention is to provide a conducting polymer having substituents that can undergo postpolymerization reactions in order to provide sites for covalent bonding of the analyte-specific probe molecules.

Another object of the present invention is to provide a conducting polymer that is stable to the analyte environment and that maintains polymer conductivity over relatively long periods of time.

Another object of the present invention is to provide a conducting polymer having substituents that can react with bridging molecules and therefore allow probe molecules to be covalently bound to the conducting polymer.

Another object of the present invention is to provide conducting polymers having reactive functionalities that are protected by blocking groups, that are unaffected by the polymerization process, and that can react with the probe molecules or bridging molecules after removal of the blocking group.

Another object of the present invention is to provide monomers that yield conducting polymers that can covalently bond to probe molecules.

Another object of the present invention is to provide monomers that yield conducting polymers exhibiting sufficient conductivity such that conductivity differences resulting from analyte interactions can be detected, measured and related to analyte concentrations.

Another object of the present invention is to provide highly conductive polymers from monomers that can undergo substituted postpolymerization covalent bonding to a probe molecule or to a bridging molecule.

Another object of the present invention is to provide heterocyclic aromatic monomers that yield highly conducting polymers and that are substituted so as to allow postpolymerization covalent bonding to a probe molecule or to a bridging molecule.

Another object of the present invention is to provide heteroaromatic monomers having a pyrrole or a thiophene ring substituted in the three-position and yielding a conducting polymer exhibiting sufficient conductivity to allow detection and measurement of an analyte in liquid media.

Another object of the present invention is to provide heterocyclic aromatic monomers consisting of two thiophene rings, two selenophene rings, or two tellurophene rings; or a two ring heteroaromatic system including a combination of a furan, a thiophene, a selenophene, and a tellurophene ring; or a two ring heteroaromatic system including a pyrrole ring in combination with a furan, a thiophene, selenophene, or tellurophene ring; wherein the pyrrole, if present, is substituted in the three-position and, if pyrrole is absent, either of the heteroaromatic rings of the monomer is substituted in the three-position.

Another object of the present invention is to provide a heterocyclic aromatic monomer including three heterocyclic aromatic compounds wherein the two terminal heteroaromatic rings of the monomer are both furan, both thiophene, both selenophene, both tellurophene or a combination of furan, thiophene, selenophene and tellurophene; and the center ring of the monomer is a three position substituted thiophene, furan, selenophene, tellurophene or pyrrole ring.

Another object of the present invention is to provide heterocyclic aromatic monomers, having one five-membered heteroaromatic ring substituted in the three-position, wherein the ring substituent can withstand the polymerization conditions, does not materially reduce the conductivity of the resulting conducting polymer, and can be reacted after polymerization to covalently bond a probe molecule or bridging molecule to the conducting polymer.

DETAILED DESCRIPTION OF THE INVENTION

These and other objects and advantages of the present invention will become apparent from the following detailed description of the invention.

In accordance with the method of the present invention, organic conducting polymers are utilized as analyte sensors in diagnostic devices to determine the presence and concentration of specific analytes in liquid media. Although organic conducting polymers have been studied extensively, the use of conducting polymers in analyte sensors has been impeded by several problems, including polymer film stability, polymer conductivity, physical characteristics of the polymer, inability to test for a specific analyte, and poor analyte detection mechanisms. As will be described more fully hereinafter, the method of the present invention, surprisingly and unexpectedly, reduces or eliminates the problems encountered in using organic conducting polymers as analyte sensors.

In accordance with the present invention, a novel class of monomers that yield highly conducting polymers has been developed. The monomers are readily polymerized, chemically or electrochemically, to yield stable polymers having sufficient conductivity for use as analyte sensors. The novel monomers, in addition to providing conducting polymers having suitable electrical and physical properties to act as an analyte sensor, also possess reactive substituent groups that can be functionalized after polymerization. In contrast to the prior art, that teaches unsubstituted pyrrole as unique because it is more easily oxidized and yields highly conducting polymers compared to ring-substituted pyrroles, it is both unexpected and surprising that the reactive substituent groups present on the monomers used in the method of the present invention do not reduce the conductivity of the resulting polymer to such an extent that the polymer is unsuitable as an analyte sensor. Even more surprisingly, it has been found that the reactive substituent can undergo postpolymerization reaction and functionalization with an analyte-specific probe molecule, such as an antigen, enzyme or ion-specific binding site, without seriously affecting the electrical properties of the polymer film.

Furthermore, it was found that the analyte-specific probe molecule can be covalently bound to the surface of the conducting polymer. As a result of the intimate, covalent contact between the probe molecule and the conducting polymer surface, the vibrational interaction resulting from the reaction between the probe molecule and the analyte can be transferred to the surface of the conducting polymer, thereby affecting the conductivity of the polymer. In effect, the vibrational interactions of the probe molecule-analyte reaction are transduced into a measurable electric signal. This electric signal then is related to the presence and/or concentration of the specific analyte in solution. This vibrational energy-conductivity change analyte sensing mechanism is both new and unexpected in the art, and occurs because of the ability to covalently bond a specific probe molecule to the surface of the conducting polymer either directly or indirectly through a bridging molecule.

In accordance with an important feature of the present invention, the problems previously encountered in utilizing conducting organic polymers as analyte sensors in diagnostic devices are reduced or eliminated by synthesizing conducting polymers from the novel class of monomers, generally depicted by structure XI:

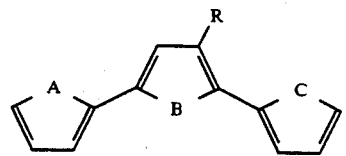

wherein A is sulfur, oxygen, selenium or tellurium, C is sulfur, oxygen, selenium or tellurium, and B is sulfur, oxygen, selenium, tellurium or N-R', wherein N is nitrogen and R' is hydrogen, an alkyl group, or a hydroxyalkyl group. R is defined hereinafter.

In accordance with another important feature of the present invention, monomers having the general structure XI yield sufficiently conducting polymers having reactive substituents capable of postpolymerization reaction and functionalization. As previously discussed, such results are surprising and unexpected in light of the dramatic decrease in conductivity found in ring-substituted polypyrroles compared to the parent polypyrrole. However, as also previously discussed, the presence of the aromatic thiophene, furan, selenophene and/or tellurophene rings adjacent to the substituted pyrrole ring sufficiently decreases the steric interaction between the ring substituent (R) and the adjacent sulfur, oxygen, selenium and/or tellurium heteroatoms.

The overall result is a class of monomers, having the general structure XI, that are essentially planar and that yield essentially planar conducting polymers having an essentially intact pi-electron system and, therefore, a relatively high conductivity. In addition, because of the same steric and electronic effects that exist in monomers having the general structure XI and because oxidation potentials drop as monomer size increases, the following monomers, illustrated by the general structures XII and XIII, also are expected to serve as suitable monomers for the synthesis of highly conducting polymers that can undergo postpolymerization reaction and functionalization without adversely affecting the conductivity of the polymer.

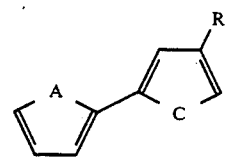

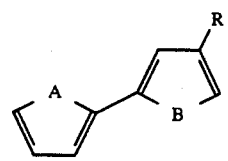

In synthesizing monomers having the general structure XI, it was found that several conflicting conditions had to be satisfied. In addition to the normal synthetic problems involved in synthesizing a three-ring monomer, such as a pyrrole ring flanked by thiophene, furan, selenophene and/or tellurophene rings, the placement of the reactive three-position substituent (R) on the central heteroaromatic ring posed several additional problems. For example, the reactive three-position substituent cannot be extremely electron-withdrawing or electron-donating because large electronic effects either could alter the oxidation potential of the monomer to such an extent that polymerization is precluded or, if polymerization was possible, could adversely affect the conductivity of the polymer. Conversely, the three-position substituent cannot be so inert, like an alkyl group, as to preclude postpolymerization reaction and functionalization of the conducting polymer.

Additionally, the reactive three-position substituent must be sufficiently stable to withstand the chemical or electrochemical polymerization process. However, the three-position substituent must be sufficiently reactive to allow the substituent to be functionalized, after polymerization, with the specific probe molecule under chemical conditions that do not attack the conducting polymer or destroy the electrical properties of the polymer. Finally, the reactive three-position substituent must be sufficiently small to allow the polymer chains to arrange themselves in sufficiently close proximity to permit charge transfer from polymer chain to polymer chain to take place.

In accordance with an important feature of the present invention, several monomers having the general structure XI, wherein A and C are sulfur and B is —NR'—, wherein R' is hydrogen, and having a reactive three-position substituent meeting the above criteria and introduced on the central ring, have been synthesized and polymerized. As seen in the following examples, the synthesis of several monomers having general structure XI was verified by the following analytical techniques.

Infrared (IR) spectra of the monomers were obtained with a Perkin-Elmer Model 710B or 237 infrared spectrophotometer, or a Nicolet 5DBXB FT IR spectrometer unless otherwise noted; the 1602 cm$^{-1}$ band of polystyrene film was used as an external calibration standard, and absorbences are reported as cm$^{-1}$.

Proton magnetic resonance ($^1$H NMR) spectra were obtained at 89.55 MHz using a JEOL FX-900 spectrometer or at 60 MHz using a Varian T-60 spectrometer. Spectra of the monomers were obtained using a deuterated chloroform (CDCl$_3$) solution, unless otherwise noted. Chemical shifts are reported in parts per million downfield from the internal standard, tetramethylsilane (TMS).

Mass spectra (MS) were obtained using a Hewlett-Packard 5985A spectrometer operating in either an electron impact (EI), chemical ionization (CI), or fast atom bombardment (FAB) mode.

During the synthesis of each monomer, commercial organic reagents were used without purification, unless otherwise noted. Inorganic reagents and reaction solvents were ACS reagent grade. Tetrahydrofuran (THF) was HPLC grade. Brine refers to a saturated aqueous sodium chloride solution.

Thin layer chromatography (TLC) was performed using silica gel 60F 254 plates from E. Merck. Flash column chromatography was performed using E. Merck or American Scientific Products Silica Gel 60 (230-400 mesh). All reported melting points and boiling points are uncorrected.

Elemental analyses were performed by Galbraith Laboratories, Inc. or by Miles Laboratories, Inc.

The synthetic scheme, including precursors, producing several of the suitable monomers having the general structure XI, is found by reference to the following examples.

EXAMPLE I

N-(2-Thienylmethyl)-2-Thienylcarboxamide (XIV)

A mixture of 12.8 g (0.1 mol) of 2-thiophenecarboxylic acid and 25 mL of thionyl chloride was stirred under reflux for 2 hours, or until hydrogen chloride and sulfur dioxide evolution stopped. The excess thionyl chloride was removed under reduced pressure by azeotroping with carbon tetrachloride (CCl$_4$), and the residue dissolved in 50 mL of diethyl ether. The resulting solution was added dropwise to a cold, stirred solution containing 11.3 g (0.1 mol) of 2-thiophenemethylamine dissolved in a mixture of 100 mL of diethyl ether and 20 mL of triethylamine.

The resulting mixture was partitioned between chloroform (CHCl$_3$) and water. The organic and aqueous phases were separated. The organic phase was washed with an 1N hydrochloric acid solution, then with a sodium bicarbonate solution. The organic phase was dried over sodium sulfate, filtered and the CHCl$_3$ evaporated to yield 21.83 g (98%) of a yellow solid. TLC (silica gel); 60:10:1 [CHCl$_3$:methanol (CH$_3$OH):concentrated ammonium hydroxide (NH$_4$OH)] showed one product.

A portion of the product was recrystallized from CHCl$_3$/diethyl ether to yield a white solid having a melting point (mp) of 115°-117° C.

Analysis: Calc'd for C$_{10}$H$_9$NOS$_2$: C,53.78; H, 4.06; N, 6.27 Found: C,53.68; H, 3.82; N, 6.48

$^1$H NMR (60 MHz, CDCl$_3$)δ: 4.7 (d, 2H, —N-H—CH$_2$—); 6.8-7.8 (m, 6H)

IR (CHCl$_3$)cm$^{-1}$: 3450, 1660, 1550

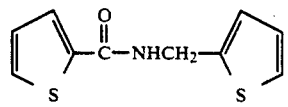

XIV

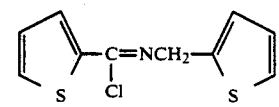

XV

EXAMPLE II

N-(2-Thienylmethyl)-2-Thienyliminochloride (XV)

A cold (0° C.) solution including 27 g of phosgene in 140 mL of CHCl$_3$ was treated with 1.5 mL of N,N-dimethylformamide (DMF), then a solution containing 15.44 g of compound XIV (69 mmol) in 100 mL of CHCl$_3$ was added dropwise over a 0.5 hour period. The resulting mixture was stirred for 1 hour at 0° C., then was allowed to warm to ambient temperature overnight (approximately 21 hours).

An aliquot of the reaction mixture was withdrawn via syringe and the solvents removed in vacuo. The resulting oil was azeotropically distilled with CCl$_4$. The product residue gave the following spectral data:

IR(CDCl$_3$)cm$^{-1}$: 1650

$^1$H NMR(60 MHz, CDCl$_3$)δ: 5.08 (s, 2H); 7.0-7.8 (m, 6H)

TLC (SiO$_2$, 9:1 toluene:dioxane): R$_f$=0.1

The solvents were evaporated at 40° C. in vacuo from the bulk of the reaction mixture to yield a dark red oil. The oil was triturated with diethyl ether and the combined filtrates filtered through CELITE (Manville Products Corp., Denver, Colo. 80217). The diethyl ether then was removed in vacuo. The compound XV was obtained by evaporative distillation at 116°–140° (0.1 mm), yielding 14.4 of XV as a light yellow oil (86%).

EXAMPLE III

3-Cyano-3-[H]-4,5-Dihydro-2,5-Dithienylpyrrole (XVI)

To a cold (−30° C.) stirred solution, protected by an inert atmosphere, containing 15.66 g of (65 mmol) compound XV and 32 g (330 mmol) of acrylonitrile in 65 mL of dry DMF was added 8.5 g of 1,5-diazabicyclo[4.3.0]non-5-ene (DBN, 66 mmol) dropwise. The resulting mixture was stirred at −30° C. for 1.5 hours. The excess acrylonitrile then was evaporated at 50° C., and 17 mm pressure. DMF was removed by evaporation at 50° C., and 0.1 mm pressure. The residue was partitioned between $CHCl_3$ and water, filtered through CELITE to remove polyacrylonitrile, and the organic and aqueous layers separated. The $CHCl_3$ layer was dried over magnesium sulfate, filtered, and evaporated. The resulting oil was dissolved in toluene and chromatographed on 200 g of $SiO_2$-60 eluted with a 1% dioxane-toluene solvent mixture. Fifteen milliliter-sized fractions were collected.

Fractions numbered 16 to 40 contained one regioisomer (analytical TLC, $SiO_2$, 1% dioxanetoluene, $R_f$=0.5 visualization with ceric ammonium nitrate spray reagent). Fractions numbered 16 to 40 were combined and concentrated to yield 6.6 g of an oil that eventually solidified (39% yield).

The following analytical data was obtained in regard to the structure of this regioisomer:

$^1$H NMR (60 MHz, $CDCl_3$)δ: 3.0–3.8 (m, 3H, pyrrole $C_3$-H, $C_4$-$H_2$); 5.68 (dd, pyrrole $C_5$-H); 7.0–7.6 (m, 6H, thienyl C—H).

An analytical sample of this regioisomer (mp 120.5°–122.5° C.) was prepared from a $CHCl_3$-hexane solvent mixture.

Analysis: Calc'd. for $C_{13}H_{10}N_2S_2$: C, 60.43; H, 3.90; N, 10.84; Found: C, 61.15; H, 4.19; N, 10.76

Mass Spectrum (EI) m/e=258.3 (M+, 45.9%) 259.0 (M+1, 9.4%)

Fractions numbered 41 through 49 were combined and concentrated to yield 0.29 g (2% yield) of an oil containing a mixture of the regioisomer found in fractions 15–40 and a second regioisomer ($R_f$=0.4). Fractions numbered 50 through 79, after combining and concentrating yielded 4.9 g of an oil containing only the regioisomer of $R_f$=0.4 and having the following spectral characteristics:

$^1$H NMR (60 MHz, $CDCl_3$)δ: 3.2–3.8 (m, 3H, pyrrole $C_3$-H, $C_4$-$H_2$) 5.8 (d, J=8Hz, pyrrole $C_5$-H); 7.0–7.6 (m, 6H, thienyl C—H)

An analytical sample of the second regioisomer (mp 105°–106°) was prepared by recrystallization from methylene chloride ($CH_2Cl_2$).

Analysis: Calc'd. for $C_{13}H_{10}N_2S_2$: C, 60.43; H, 3.90; N, 10.84 Found: C, 55.54; H, 3.78; N, 9.99 (12% $CH_2Cl_2$)

Mass Spectrum (EI) m/e=258 (M+, 30%).

In all later syntheses, the crude reaction mixture, containing both diastereomers, was used without further purification.

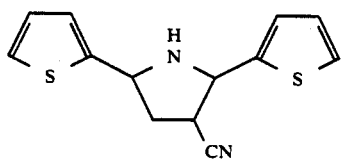

XVI

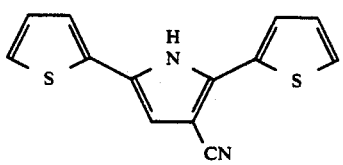

XVII

EXAMPLE IV

3-Cyano-2,5-Dithienylpyrrole (XVII)

A solution containing 13.05 g of crude 3-cyano-3-[H]-4,5-dihydro-2,5-dithienylpyrrole (XVI) and 2.9 g of 10% Pd/C in 135 mL of diphenyl ether was heated at 195° C. for 5 hours under a purging stream of carbon dioxide ($CO_2$). The reaction mixture then was cooled and subsequently filtered through CELITE. The filter cake was washed with $CHCl_3$ and the combined filtrates were evaporated in vacuo first at 12 mm pressure, then at 1.2 mm pressure, to remove the reaction solvents. The residue (10.14 g) was recrystallized from an acetone-toluene mixture to yield 3.14 g of the product XVII (24.2% yield) as a greyish-yellow solid (mp 202°–203.5° C.).

Analysis: Calc'd. for $C_{13}H_8N_2S_2$: C, 60.91; H, 3.15; N, 10.93 Found: C, 61.16; H, 3.26; N, 11.06

The mother liquor was concentrated to give 8.08 g of a viscous oil that was flash chromatographed on 250 g of $SiO_2$ eluted with a 19:1 toluene-THF solvent mixture. Fractions numbered 36 through 64, containing the reaction product, were combined, then concentrated, to yield 2.5 g of a yellow solid that was recrystallized from acetone-toluene to give an additional 1.26 g of compound XVII (9.7% yield). An additional 489 mg of the compound XVII was similarly obtained from the mother liquor (3.8% yield) by repeating the above procedure. The total isolated yield of compound XVII was therefore 37.7%.

IR (KBr) $cm^{-1}$: 3210, 3160, 2210

$^1$H NMR (90 MHz, DMSO-$d_6$)δ: 6.8 (d, J=2 Hz, 1H); 7.1 (q, J=4 Hz, 2H); 7.46 (d, J=4 Hz, 2H); 7.7 (d, J=4 Hz, 2H).

$^{13}$C NMR (22.5 MHz, DMSO-$d_6$)δ: 90.1, 109.8, 116.7, 124.0, 125.0, 126.0, 126.7, 127.8, 128.2, 131.2, 133.2, 133.7

Mass Spectrum (EI) m/e: 256.3 (M+, 100.0%) 257.1 (M+1, 22.4%).

EXAMPLE V

3-Aminomethyl-2,5-Dithienylpyrrole (XVIII)

To a stirred solution of 0.8 g (3 mmol) of 3-cyano-2,5-dithienylpyrrole (XVII) in 20 mL of dry THF was added 8 mL of a 1M solution of borane-tetrahydrofuran complex in THF. After the initial exothermic reaction subsided, the mixture was heated to reflux under an inert (argon gas) atmosphere overnight. The solvents then were evaporated in vacuo and the residue partitioned between $CHCl_3$ and a 3N hydrochloric acid (HCl) solution. The $CHCl_3$ layer then was extracted three times with 10 mL portions of 3N HCl dried over sodium sulfate, filtered, and concentrated in vacuo to give 410 mg of unreacted 3-cyanodithienylpyrrole (XVII).

The combined aqueous acidic solutions were made basic with a sodium hydroxide (NaOH) solution and then were extracted with $CHCl_3$. The resulting $CHCl_3$ solution was dried over magnesium sulfate, filtered, and concentrated to yield 360 mg of a solid. Recrystallization of the solid from hot toluene gave 100 mg of compound XVIII (mp 154°-155° C.).

Analysis: Calc'd. for $C_{13}H_{12}N_2S_2$: C, 59.96; H, 4.65, N, 10.76 Found: C, 59.99; H, 4.61; N, 10.5

$^1$H NMR (60 MHz, $CDCl_3$)δ: 3.8 (s, 2H); 1.95 (m, 3H); 6.5 (s, 1H); 7.1-7.3 (m, 6H)

Mass Spectrum (EI) m/e: 260.1 ($M^+$, 100%), 244.1 ($M^+$—$NH_2$, 100%).

The mother liquor was concentrated and chromatographed by preparative TLC plates ($SiO_2$-60, 20 cm×20 cm×1000u) eluted successively with $CHCl_3$ and a 60:5:1 $CHCl_3$-$CH_3OH$-concentrated $NH_4OH$ solvent mixture. The chromatographic band containing the product XVIII was excised and extracted with hot ethanol. The ethanol solution was filtered, then concentrated in vacuo to yield an additional 100 mg of compound XVIII. The combined yield of compound XVIII was 460 mg (59% yield).

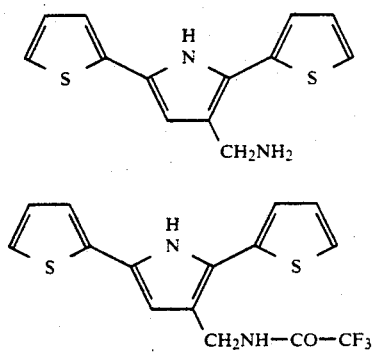

XVIII

XIX

EXAMPLE VI

3-N-Trifluoroacetamidomethyl-2,5-dithienylpyrrole (XIX)

A mixture containing 1.64 g (6.31 mmol) of 3-aminomethyl-2,5-dithienylpyrrole (XVIII) in 75 mL of $CHCl_3$ was cooled to 0° C. and treated successively with 7.5 mL of ethyl trifluoroacetate and 1.0 mL of diisopropylethylamine. The mixture was allowed to warm to ambient temperature and produced a homogenous solution. After two hours at ambient temperature, an additional 2 mL of ethyl trifluoroacetate and 0.5 mL of diisopropylethylamine was added to the mixture. The mixture was stirred overnight, then heated to reflux for ten minutes. After cooling, the mixture was concentrated in vacuo to yield an oil. The residual oil was flash chromatographed on 250 g of $SiO_2$-60 (230-400 mesh) eluted with $CHCl_3$. Eighteen milliliter-sized fractions were collected, and fractions numbered 18 through 42 were combined and concentrated to yield 2.11 g of a brown foam. Recrystallization of the brown foam, with seeding, from a 2:1 toluene-hexane mixture, gave 1.51 g (70% yield) of a pink-beige powder (mp 107°-109° C.).

Analysis: Calc'd. for $C_{15}H_{11}F_3N_2OS_2$: C, 50.55; H, 3.11; N, 7.86 Found: C, 50.47; H, 3.12; N, 7.54

$^1$H NMR (90 MHz, $CDCl_3$)δ: 4.55 (d, J=5Hz, 2H); 6.40 (m, NH); 6.42 (d, pyrrole $C_2$-H); 7.0-7.3 (m, 6H); 8.4 (m, NH)

$^{13}$C NMR (22.5 MHz, $CDCl_3$)δ: 36.7, 108.7, 117.1, 121.9, 123.6, 124.4, 124.8, 125.0, 127.4, 127.8, 133.0, 134.8

IR (KBr) $cm^{-1}$: 3300, 3100, 1700, 1550, 1210, 1190, 1170.

EXAMPLE VII 3-(2-Hydroxyethyl)-2,5-Dithienylpyrrole (XX)

A solution containing 2.31 g (10 mmol) of 2,5-di(2-thienyl)pyrrole (VI) in 100 mL of dry diethyl ether, maintained at 0° C., was treated with 6.3 mL of a 1.6M solution of n-butylmagnesium bromide (10 mmol) in diethyl ether. The resulting slurry was stirred for 0.5 hour at 0° C. and then was treated with 3 g of ethylene oxide. The mixture was stirred for 1 hour at 0° C. Dry THF (100 mL) was added to produce a homogeneous solution and the solution was stirred for 1 hour at 0° C. The solution was allowed to reach ambient temperature over 1 hour period, then the reaction was quenched by adding 1 mL of a saturated ammonium chloride ($NH_4Cl$) solution. The resulting mixture was filtered, and the solvents evaporated in vacuo in the presence of 25 g of $SiO_2$-60. The solid absorbed on the $SiO_2$-60 was chromatographed on a 200 g column of $SiO_2$-60 using a 1% dioxane-toluene solvent mixture. Fractions of 15 mL in volume were taken. Fractions numbered 111 through 215 were combined and concentrated to yield 1.36 g of an oil, containing of a mixture of the desired compound XX and approximately 17% of a contaminant identified as N-(2-hydroxyethyl)-2,5-di(2-thienyl)-pyrrole, as determined by $^1$H NMR. The mixture was used without further purification.

$^1$H NMR (60 MHz, $CDCl_3$)δ: 3.0 (t, J=6Hz, pyrrole-$C_3$-$CH_2$-$CH_2$-OH); 3.4 (m, N-$CH_2$-$CH_2$-OH); 3.9 (t, J=6Hz, pyrrole-$C_3$-$CH_2$); 4.4 (t, J=6Hz, N-$CH_2$-); 6.4 (d, J=2Hz); 6.9-7.4 (m, 6H); 8.93 (m, NH)

Mass Spectrum (EI) m/e 275.1 ($M^+$, 56.3%)

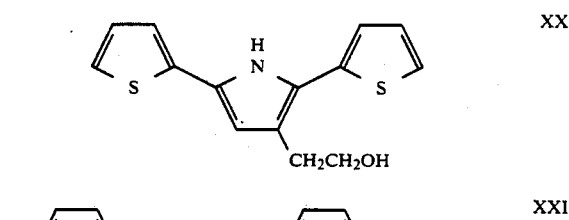

XX

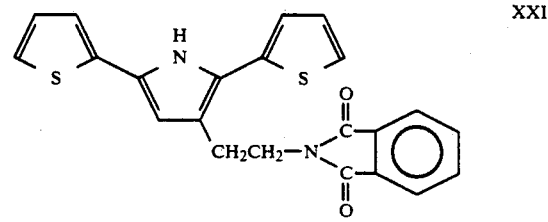

XXI

EXAMPLE VIII 3-(2-Phthalimidoethyl)-2,5-dithienylpyrrole (XXI)

A solution containing 0.75 g of methanesulfonyl chloride in 25 mL of $CH_2Cl_2$ was added to a stirred solution containing 0.8 g (3.3 mmol) of 3-(2-hydroxyethyl)-2,5-dithienylpyrrole (XX) and 3 mL of triethylamine in 25 mL of methylene chloride (CH$_2$Cl$_2$) maintained at 0° C. under an inert argon gas atmosphere. The mixture was stirred for 2 hours at 0° C., followed by treatment with a solution containing 8 g (40 mmol) of potassium phthalimide in 50 mL of DMF. The resulting mixture was heated at 40° C. overnight. After cooling to room temperature, the mixture was filtered, and the solvents of the filtrate evaporated in vacuo in the presence of with 20 g of SiO$_2$-60. The solid absorbed on the SiO$_2$ was chromatographed on a 100 g column of SiO$_2$-60 that was equilibrated and eluted with a 1% dioxane-toluene solvent mixture. Fractions having volumes of 20 mL were collected, and fractions numbered 10 through 25, containing the product (XXI), were combined, then concentrated to yield 860 mg of an oil (64% yield). An analytical sample of compound XXI (mp 174°–175° C.) was recrystallized from diethyl ether.

Analysis: Calc'd. for C$_{22}$H$_{16}$N$_2$O$_2$S$_2$: C, 65.32; H, 3.99; N, 6.93 Found: C, 65.06; H, 4.03; N, 6.71

$^1$H NMR (60 MHz, CDCl$_3$)δ: 3.0 (t, J=7Hz, 2H); 3.9 (t, J=7Hz, 2H); 6.4 (d, J=3Hz, 1H); 6.9–7.3 (m, 6H); 7.7 (m, 4H); 8.5 (m, NH)

IR (CHCl$_3$)cm$^{-1}$: 3450, 3010, 1780, 1720, 1405, 1370
Mass Spectrum (EI) m/e: 404.1 (M$^+$, 39.4%) 405 (M$^{+1}$, 11.2%)

EXAMPLE IX 3-(2-Aminoethyl)-2,5-dithienylpyrrole (XXII)

A solution of 800 mg of 3-(2-phthalimidoethyl)-2,5-dithienylpyrrole (XXI) and 100 mg. of 95% hydrazine (3 mmol) in 25 mL of ethanol was heated to reflux for 3 hours. The mixture then was cooled and diluted with 25 mL of 1N HCl. The ethanol was removed in vacuo, and the resulting aqueous solution was filtered. The filtrate was made alkaline with sodium hydroxide (NaOH) and extracted with CHCl$_3$. The organic CHCl$_3$ layer was dried over magnesium sulfate, filtered, and the CHCl$_3$ evaporated to give 0.48 g of a yellow oil. The product was isolated by preparative SiO$_2$ TLC (20 cm×20 cm×1000u) using a 120:10:1 CHCl$_3$-CH$_3$OH-conc.NH$_4$OH solvent mixture. Three hundred mg of a solid was obtained. The solid was recrystallized from a toluene-hexane solvent mixture and dried at 55° C. at 0.1 mm pressure gave 200 mg of compound XXII (24% yield, mp 136°–138° C.).

Analysis: Calc'd. for C$_{14}$H$_{14}$N$_2$S$_2$: C,61.28; H, 5.14; N, 10.21 Found: C,61.20; H, 5.15; N, 9.81

$^1$H NMR (60 MHz, CDCl$_3$)δ: 2.0 (m, NH$_2$); 2.8 (m, 4H); 6.3 (s, 1H); 6.8–7.4 (m, 6H)

IR (CHCl$_3$)cm$^{-1}$: 3430, 2920, 1590, 1520, 1430, 1270
Mass Spectrum (EI) m/e: 274.0 (M$^+$, 35%)

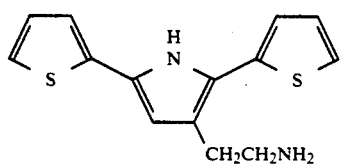

XXII

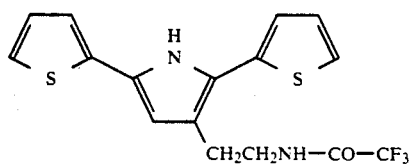

XXIII

EXAMPLE X 3-(2-Trifluoroacetamidoethyl)-2,5-dithienylpyrrole (XXIII)

A solution containing 100 mg (0.36 mmol) of 3-(2-aminoethyl)-2,5-dithienylpyrrole (XXII), 2 mL of ethyl trifluoroacetate, and 5 mL of CHCl$_3$ was allowed to stand at ambient temperature overnight. The CHCl$_3$ solvent was removed in vacuo, and the product XXIII isolated by preparative SiO$_2$-TLV plates (20 ×20 ×1000u) eluted with a 9:1 toluene-dioxane solvent mixture. Sixty mg of compound XXIII was obtained (45% yield).

$^1$H NMR (60 MHz, CDCl$_3$)δ: 2.87 (t, 2H); 3.5 (t, 2H); 6.26 (d, 1H, pyrrole C$_3$-H); 6.8 (m, 1H, NH); 7.0 (m, 6H); 8.4 (m, NH)

Mass Spectrum (EI) m/e: 370.2 (M$^+$, 75.9%).

EXAMPLE XI

3-Acetyl-2,5-Dithienylpyrrole (XXIV)

A mixture containing 13.25 g (53 mmol) of 1,4-dithienyl-1,4-butanedione, 38.9 g (0.53 mol) of ammonium acetate, 53 mL of acetic anhydride, and 212 mL of acetic acid was stirred under reflux in an inert argon gas atmosphere for 12 hours. The solvents then were removed in vacuo and the residue partitioned between CHCl$_3$ and water. The organic and aqueous layers were separated and the organic solvents evaporated in vacuo to yield a solid. Analytical TLC showed that the solid was a mixture of starting materials and several reaction products. The crude solid was dissolved in a mixture containing 38.9 g of ammonium acetate, 106 mL of acetic anhydride, and 212 mL of acetic acid and heated to reflux overnight. The resulting mixture was cooled and concentrated by removing the solvents in vacuo. The residue was partitioned between diethyl ether and water. A solid precipitated from the aqueous layers, and the solid was filtered, dried, and found to be unreacted starting material diketone (8.6 g). The filtrate and the diethyl ether layer were found to contain a mixture of three components. The diethyl ether layer was dried over magnesium sulfate, filtered, and the ether removed in vacuo to yield a dark oil. Crystallization of the oil from toluene yielded 1 g of a solid identified as 3-acetyl-2,5-dithienylpyrrole (XXIV), mp 181°–183° C.

Analysis: Calc'd. for C$_{14}$H$_{11}$NOS$_2$: C,61.51;H,4.06; N,5.12 Found: C,61.43; H,4.31; N,5.02

$^1$H NMR (60 MHz, CDCl$_3$)δ: 2.39 (s, 3H); 6.78 (d, J=3Hz, 1H, pyrrole C$_3$-H); 6.95–7.4 (m, 5H); 7.55 (dd, J=3Hz, 1H); 9.07 (m, NH)

IR (CDCl$_3$)cm$^{-1}$: 3400, 3200, 1668
Mass Spectrum (EI) m/e: 273.0 (M$^+$, 82.3%).

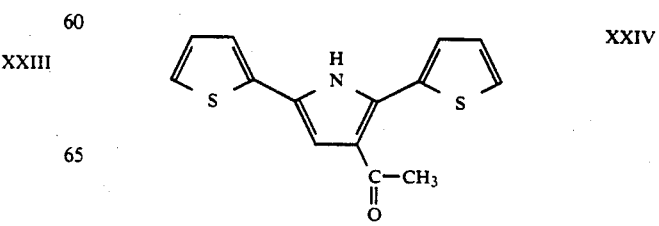

XXIV

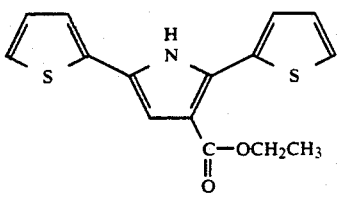 XXV

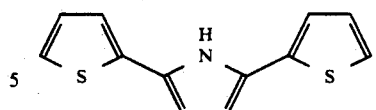 XXVI

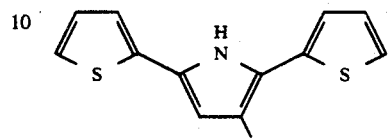 XXVII

EXAMPLE XII

3-Carboxyethyl-2,5-Dithienylpyrrole (XXV)

A mixture containing 22.42 g (93 mmol) of N-(2-thienylmethyl)-2-thienyliminochloride (XV), 10.8 g (110 mmol) of ethyl propiolate, 12.5 g of freshly distilled DBN, and 150 mL of dry DMF was stirred at 0° C. for 0.5 hour, then allowed to warm to ambient temperature over a 3.5 hour period. The reaction solvents were removed in vacuo at 50° C. and the residue dissolved in $CH_2Cl_2$. The organic mixture was washed successively three times with 5% aqueous HCl, water, and 5% aqueous $NaHCO_3$. After drying over magnesium sulfate, filtering and removing the organic solvents in vacuo, the resulting oil was distilled. The fraction distilling at 190°-220° C. was chromatographed on a 100 g column of $SiO_2$-60 eluted with toluene. Fractions numbered 31 through 95, 15 ml in each volume, contained the desired compound (XXV) ($R_f$=0.27). The fractions were combined, then concentrated to yield 2.5 g of an oil. Crystallization of the oil from hexane gave 600 mg of compound XXV (2% yield, mp 103°-104° C.).

Analysis: Calc'd. for $C_{15}H_{13}NO_2S_2$: C, 59.38; H, 4.32; N, 4.62 Found: C, 59.13; H, 4.46; N, 4.51

$^1$H NMR (60 MHz, $CDCl_3$)δ: 1.45 (t, J=7Hz, 3H); 4.55 (q, J=7Hz, 2H); 6.88 (d, J=3Hz, 1H); 7.0-7.6 (m, 5H); 7.65 (dd, J=3Hz, 1Hz, 1H)

IR (KBr) $cm^{-1}$: 3430, 2970, 1700, 1600, 1450, 1260, 1115.

EXAMPLE XIII

3-[(N-3-Carbomethoxypropionyl)aminomethyl]-2,5-Dithienylpyrrole (XXVI)

To a solution of 400 mg (1.54 mmol) of 3-aminomethyl-2,5-dithienylpyrrole (XVIII) and 378 ul (3.07 mmol) of diisopropylethylamine in 15 ml of anhydrous methylene chloride was added 3-carbomethoxypropionyl chloride (1.6 ml, 9.23 mmol). After stirring for 5 minutes at room temperature, the reaction mixture was quenched by the addition of 1 ml of water. The aqueous layer was extracted three times with 5 ml portions of chloroform and the combined organic layers were dried over anhydrous magnesium sulfate, filtered, and concentrated in vacuo. The crude reaction product was chromatographed on 100 g of silica gel. Elution with chloroform:methanol, 95:5, gave 456 mg (39%) of the amide (XXVI) as a greenish solid having a mp of 48°-49° C., and $R_f$:0.55 (chloroform:methanol, 98:2).

IR (KBr)$cm^{-1}$: 3400, 1735, 1650, 1530, 1440, 1220, 1170, 860, 695

$^1$H NMR ($CDCl_3$, 60$MH_z$)δ: 6.90 to 7.36 (m, 7H); 6.42 (M, 1H, pyrrole C4-H); 5.70 to 6.00 (brs, 1H, -NH-); 4.33 to 4.63 (M, 2H, $\underline{CH_2}$-N); 3.67(s, 3H, -$\underline{CO_2CH_3}$); 2.60 (t, 2H, J=5Hz -$\underline{CH_2}$-CO-); 2.51 (t, 2H, J=5$H_z$, -$\underline{CH_2}$CO)

Mass spectrum (EI) m/e: 374.2 ($M^+$, 100%).

EXAMPLE XIV

3-[(N-3-Carboxypropionyl)-aminomethyl]-2,5-Dithienylpyrrole (XXVII)

A mixture of compound XXVI (200 mg, 0.53 mmol), 0.6N aqueous sodium hydroxide (1.34 ml, 0.80 mmol) and 4 ml of methyl alcohol was stirred at room temperature for 16 hours. The reaction mixture was poured onto 15 ml of ice water and was washed with diethyl ether. The aqueous layer was acidified with 1N aqueous hydrochloric acid to pH 4.0, then saturated with sodium chloride. The saturated solution then was extracted four times with 5 ml portions of ethyl acetate. The combined organic extracts were washed with the 5 ml portions of water, dried over anhydrous magnesium sulfate, then filtered. Evaporation of solvent in vacuo gave a crude acid that was then purified on 20 g of silica gel. Elution with ethyl acetate:acetic acid, 95:5, provided 121 mg (63%) of acid (XXVII), having $R_f$:0.28 (ethyl acetate:acetic acid, 95:5).

IR (KBr)$cm^{-1}$: 2700-3400, 1715, 1640, 1535, 1410, 1210, 1175, 1020, 1000, 840, 820, 690.

$^1$H NMR ($CDCl_3$, 60 $MH_z$)δ: 9.90 to 10.36 (brs, 1H, $CO_2H$); 9.63 to 9.90 (brs, 1H, -NH); 6.83 to 7.33 (m, 7H); 6.33 (d, 1H, J=3$H_z$, pyrrole C-4 protons); 4.43 (d, 2H, J=2Hz, $CH_2$-NH); 2.26 to 2.70 (m, 4H, -CO-$\underline{CH_2}$-$CH_2$CO-)

Mass spectrum (EI) m/e: 360.1 ($M^+$, 55.9%), 260.1 ($M^+$-$CO(CH_2)_2CO_2H$, 70%), 244.1 ($M^+$-$NH_2$-$CO(CH_2)_2CO_2H$, 100%).

From the above examples, it is seen that a number of different substituent groups (R) can be introduced into the three-position of the central heteroaromatic ring of the monomer. In particular, the examples show that the three-position substituent on monomers having the general structure VII can be carboxyethyl (XXV), acetyl (XXIV), cyano (XVII), aminomethyl (XVIII), aminoethyl (XXII), N-trifluoroacetamidomethyl (XIX) and N-trifluoracetamidoethyl (XXIII). However, in accordance with the method of the present invention, other substituents can be introduced into the three-position of the molecule. It also is possible to place substituents on the 4-position of the molecule, if such substituents do not materially affect the polymerizability of the monomer and the conductivity of the polymer.

To achieve full advantage of the present invention, it is necessary to have the exposed amino functionality of the monomer 3-aminomethyl-2,5-dithienylpyrrole (XVIII) available on the surface of the conducting polymer. This amino functionality is ideally suited to either covalently bond directly to an enzyme, antigen or other specific binding molecule, or covalently bond to a spacer or bridging molecule before subsequent bonding to the enzyme, antigen, or other specific binding molecule. The introduction of the exposed amino moiety on the surface of the conducting polymer can be effected either directly by polymerization of the monomer XVIII, or by polymerization of a monomer wherein the amino functionality is protectively blocked, followed by removal of the blocking group to expose the amino moiety on the polymer surface. The preferred monomer that includes the blocked amino functionality is 3-N-trifluoroacetamidomethyl-2,5-dithienylpyrrole (XIX). The monomer XIX is preferred not only because of its ease of synthesis and facile polymerization, but also because the monomer XIX affords polymers exhibiting unusual and surprising conductivity, even in comparison to polymers grown from monomer XVIII. In addition, protectively blocking the amino group enables polymer growth to be conducted in electrolyte solutions containing ions such as tetrachlororuthenate ($RuCl_4^-$). It is not possible to grow a polymer from the free amine monomer (XVIII) in the presence of tetrachlororuthenate ions because of adduct formation.

Other amino protecting groups providing better stability in the event of extreme acid or base conditions also can be used according to the method of the present invention. The protecting groups listed in Table 1 can be cleaved from the conducting polymer under conditions that are milder than the conditions required to remove the N-trifluoroacetyl group. Therefore, if necessary, the conducting polymer is protected from the relatively harsh conditions required to remove the N-trifluoroacetyl group.

efficient covalent attachment of the probe molecule, like an enzyme or an antigen, to the conducting polymer. However, the additional steric bulk of these longer spacer arms may adversely affect the growth of the polymeric film and the conductivity properties of the polymeric film. Examples of other longer spacer arm derivatives of 3-aminomethyl dithienylpyrrole are shown in Table 2.

TABLE 2
FUNCTIONALIZED SPACER ARM DERIVATIVES OF 3-AMINOMETHYL DITHIENYLPYRROLE

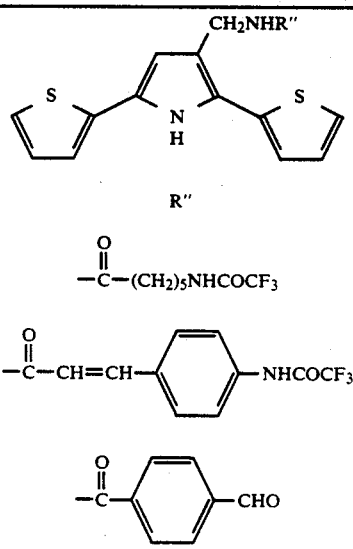

TABLE 1
AMINE N-PROTECTING GROUPS

| PROTECTING GROUP | STRUCTURE | DEPROTECTION CONDITIONS |
|---|---|---|
| N-Dithiasuccinoyl | (structure: S—C(=O)—N—C(=O)—S ring) | Thioethanol/Triethanolamine 25° C., 5 min. |
| Vinyl Carbamate | $CH_2=CH-O-C(=O)-NH-$ | Anhydrous hydrogen chloride/dioxane, 25° C.; or hydrogen bromide/acetic acid |
| t-Butyl Carbamate | $(CH_3)_3C-O-C(=O)-NH-$ | 3M Hydrochloric acid/ethyl acetate 30 min.; trifluoroacetic acid 0° C., 5 min; iodotrimethylsilane, $CHCl_3$ or acetonitrile 25° C., 6 min. |
| o-Nitrothiophenol | (o-nitrophenyl)-S-NH- | 22° C., 1 hr.; 2-mercaptopyridine, $CH_2Cl_2$, 1 min.; acetic acid, aqueous alcohol or hydrochloric acid, alcohol, 1 hr. |
| N-Trifluoracetamide | $CF_3-C(=O)-NH-$ | Sodium methoxide/ methanol 25° C., 16 hrs. |

Similarly, in accordance with the method of the present invention, monomers having a longer N-functionalized amido spacer, or bridging arm, than the 3-aminomethyl dithienylpyrrole (XVIII) can be synthesized and polymerized. Conducting polymer films synthesized from the monomers having longer spacer arms, like monomers XXVI and XXVII, allow for the more The method of the present invention allows antigen or enzyme immobilization on other dithienylpyrrole derivatives in addition to the 3-aminomethyl dithienylpyrrole derivative (XVIII). For example, the 2-hydroxyethyl derivative (XX) can be modified to provide protected and polymerizable thiol, carboxaldehyde, or carboxylate monomers. Additionally, unprotected hydroxyethyl dithienylpyrrole (XX) yields a conducting film capable of surface modification by either aminopropylsilation or oxidative chemical treatment prior to probe molecule attachment.

In accordance with the method of the present invention, conducting polymers can be synthesized from monomers having a pyrrole as the central heteroaromatic ring, and also from terthienyl monomers (structure XI, wherein A, B and C are sulfur) that are substituted at the three-position of the central thiophene ring. In general, the terthienyl monomers will yield conducting polymers having increased chemical stability making them especially useful in the preparation of conducting polymers that subsequently will be subjected to strongly alkaline conditions. Similarly, other heteroaromatic monomers, having a three-position substituted selenophene, tellurophene or furan ring as the central heteroaromatic ring of structure XI, can be used to synthesize conducting polymers.

Furthermore, in addition to the three-position substituents placed on the heteroaromatic monomer of general structure VII and described in the previous Examples, other reactive substituents that can be placed at the three-position of the heteroaromatic ring and that can be covalently bound to a probe molecule without adversely affecting the conductivity of the polymer include:

approximately four monomer units per anion, thereby producing the polymer in its oxidized state.

Electrochemical techniques can be used to drive the anion from the polymer to yield an insulating, non-oxidized polymer; and similarly electrochemical techniques can be used to oxidize, or introduce the anion, to an insulating, non-oxidized polymer. The ability to reversibly oxidize conducting polymers is extremely important and is directly connected to the stability of the conducting polymer. It should also be noted that electrochemical synthesis of the conducting polymer is preferred because the thickness of the conducting polymeric film can be easily and precisely controlled by monitoring the electrolysis time. In regard to stability, it is preferred that the conducting organic polymer is stable in the presence of water and under prolonged water exposure because a majority of the analytes of interest exist in aqueous media.

The conducting polymer films made according to the method of the present invention were synthesized electrochemically. The usual conditions for polymer synthesis involve growth of the conducting polymer under an argon gas atmosphere at an anodic potential of 0.8 V with respect to silver/silver ion $(Ag/Ag^+)$ reference electrode in an $5 \times 10^{-3}M$ monomer solution in dry acetonitrile $(CH_3CN)$ solvent that has been purged with argon gas (Ar). The dopant counterion is present at a concentration of 0.01M.

In general, the electropolymerization process re-

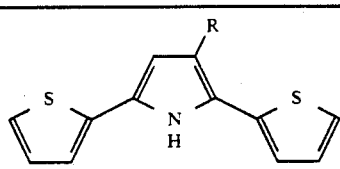

VII

| Derivative of VII | R-Group | Reactive With |
|---|---|---|
| 3-(2-methyldithioethyl) | $-CH_2CH_2-S-SCH_3$ | HS-(Protein, Fab, Enzyme) |
| 3-(N-imidazocarbonyl)amidomethyl | $-CH_2-NH-\overset{O}{\underset{\|}{C}}-N\diagup\diagdown N$ | $NH_2$-Protein |
| 3-(4-nitrophenylcarbamoyl)amidomethyl | $-CH_2NH\overset{O}{\underset{\|}{C}}O-\bigcirc-NO_2$ | $NH_2$-Protein |
| 3-(formylmethyl) | $-CH_2-CHO$ | $NH_2$-Protein (with or without Glutaraldehyde) |
| 3-(carboxymethyl) | $-CH_2-CO_2H$ | $NH_2$-Protein water soluble carbodiimide |

In accordance with another important feature of the present invention, the 2,5-di(2-thienyl)pyrrole monomers previously described can be chemically or electrochemically polymerized to yield conducting organic polymers. In the preferred synthetic method, the conducting polymer is synthesized electrochemically in order to obtain the polymer directly in its oxidized state. During the electrochemical synthesis, the conducting polymer incorporates the anion of the supporting electrolyte into the polymer structure, usually in a ratio of quires a working electrode and an electrolytic medium that includes the monomer, an organic solvent and a supporting electrolyte. The conducting polymer, in its doped and oxidized state, is grown on the working electrode. The working electrode can be a metal, such as gold, platinum, aluminum, rhodium, titanium, tantalum, nickel or stainless 314; a metal oxide such as tin oxide, titanium oxide, or indium tantalum oxide; semiconducting substances such as silicon, germanium, gallium arsenide, cadmium sulfide or cadmium selenide;

carbonaceous substances, such as graphite or glassy carbon; or other suitable electrode materials.

The choice of solvent for the electrolyte medium directly affects the physical, morphological and electrical characteristics of the conducting polymer. If an organic solvent is employed, it is preferred that the solvent be both aprotic and a poor nucleophile in order to ensure that the solvent itself does not become directly involved in the electrolytic reactions. Typical solvents that have been used in the electrochemical synthesis of the conducting polymers of the present invention include acetonitrile, tetrahydrofuran, methylene chloride, benzonitrile, dimethyl sulfoxide, ethanol, propylene carbonate, hexamethylphosphoramide, butanone and nitromethane.

The supporting electrolyte is a critical component in the electrolyte medium because the supporting electrolyte is directly incorporated into the conducting polymer as a dopant that compensates the charge carriers of the organic polymer. If the conducting polymer is grown electrochemically, the inclusion of the anionic dopant within the conducting polymer film is a direct and integral part of the polymer growth process. The conducting polymer film, as grown, is fully doped, with the anionic electrolyte included within the conducting polymer at amounts ranging from about 10 to about 35 atomic percent. The conducting polymer film, once grown, can be reversibly reduced and reoxidized with the release and reinclusion of the dopant counterions by the film attending the reduction and oxidation processes.

Electrochemical synthesis of the conducting polymer permits the selection of a particular counterion from a wide variety of electrolytes. The choice of the supporting electrolyte is important because the electrolyte will affect both the electroactivity and the structural properties of the conducting polymer film. For example, polypyrrole exhibits a conductivity that varies over five orders of magnitude by merely changing the counterion of the electrolyte.

Depending upon the desired physical and electrical properties of the polymer, several supporting electrolytes can be used according to the method of the present invention. The cation of the supporting electrolyte is most preferably a tetraalkylammonium ion, with the alkyl groups having from one to ten carbon atoms. Typical examples include tetraethylammonium and tetrabutylammonium. These tetraalkylammonium ions are especially useful because they are soluble in aprotic solvents and are highly dissociated in solution. For similar reasons, lithium is often used as the cation of the supporting electrolyte.

The anion of the supporting electrolyte can be any anion that is essentially non-nucleophilic and that is not easily oxidized. Unsuitable anions, because of excessive nucleophilicity or facile oxidation, include the halides, hydroxyl, alkoxys, cyanide, acetate and benzoate. However, most other anions, organic and inorganic in structure, can be used in the electrochemical synthesis of the conducting polymers of the present invention. Suitable anions include tetrafluoroborate ($BF_4^-$), perchlorate ($ClO_4^-$), tetrachloroferrate III ($FeCl_4^-$), tetrachlororuthenate ($RuCl_4^-$), p-toluenesulfonate, picryl sulfonate, hexafluoroarsenate, trifluoromethylsulfonate ($CF_3SO_3^-$), hexafluorophosphate ($PF_6^-$), fluorosulfonate, trifluoroacetate ($CF_3CO_2^-$), p-bromobenzenesulfonate, and perruthenate ($RuO_4^{-2}$). Similarly, metals such as iron, cobalt, nickel, ruthenium, rhodium, platinum, osmium, iridium and palladium, when positioned as the central atom of an anion, like cobalt in porphyrin or iron in iron phthalocyanin, can be used as the anion of the supporting electrolyte.

Several enzymatically-based sensor systems involve the generation of hydrogen peroxide as a secondary product. An example of such a system is the detection of glucose using glucose oxidase. To achieve the full advantage of the analyte/probe systems of the present invention, tetrachlororuthenate ($RuCl_4^-$) is used as the anion of the supporting electrolyte. This ruthenium-based anion, or similar iron-based anions, serve not only as a compensating dopant for the polymer but also as catalyst for the oxidative decomposition of hydrogen peroxide. The importance of this catalytic effect will be discussed more fully hereinafter in regard to the detection of a specific analyte, glucose.

In addition to glucose oxidase, oxidase enzymes that employ oxygen as a mediator, and therefore produce hydrogen peroxide include:
glucose oxidase,
cholesterol oxidase,
aryl-alchol oxidase,
L-gulonolactone oxidase,
galactose oxidase,
pyranose oxidase,
L-sorbase oxidase,
pyridoxin 4-oxidase,
alcohol oxidase,
L-2-hydroxyacid oxidase,
pyruvate oxidase,
oxalate oxidase,
glyoxylate oxidase,
dihydro-orotate oxidase,
lathosterol oxidase,
sarcosine oxidase,
N-methylamino-acid oxidase,
$N^6$-methyl-lysine oxidase,
6-hydroxyl-L-nicotine oxidase,
6-hydroxy-D-nicotine oxidase,
nitroethane oxidase,
sulphite oxidase,
thiol oxidase,
cytochrome c oxidase,
Pseudomonas cytochrome oxidase,
ascorbate oxidase,
o-aminophenol oxidase, and
3-hydroxyanthranilate oxidase.

As a result, in accordance with the methods of the present invention, analyte sensors can be made utilizing any oxidase enzyme by employing the same method described above for the glucose oxidase embodiment.

In the electrochemical polymerization of the monomers of the present invention, a voltage of 0.8 was found to be a useful general value. However, this voltage is not necessarily an optimal value because the threshold voltage for a majority of the monomers used to synthesize conducting polymers is considerably below 0.8 volts.

The conductivity of the polymer films grown from the substituted 2,5-di(2-thienyl)pyrrole monomers generally varied between $10^{-3}$ S/cm and approximately 0.05 S/cm, as measured using an Alessi Industries four point probe at a constant current of 15.0uA (microamperes). Films having a conductivity of less than $1 \times 10^{-2}$ S/cm required the use of a lower constant current.

This relatively high conductivity is important because the conductivity of the polymer film is directly related to the conductivity of the diagnostic device. In particular, it was found that polymer films grown from the trifluoroacetyl blocked amines of structure (XIX) exhibited the highest conductivity. The conductivities observed for the polymer films generated from the substituted 2,5-di(2-thienyl)pyrrole monomers were significantly higher than the conductivity of any derivatized polymer films reported in the prior art. Moreover, the stability of the conducting polymers generated from the substituted 2,5-di(2-thienyl)pyrrole monomers is significantly improved in comparison to the prior art derivatized films.

In general, the morphology and electrical properties of the conducting polymer depends upon the monomer, the supporting electrolyte and the polymer film thickness. For example, the following procedure illustrates the general preparation of a conducting polymer film from the dithienylpyrrole derivative, 3-N-trifluoroacetamidomethyl-2,5-dithienylpyrrole (XIX). The polymerization of this monomer, and the other 3-substituted 2,5-di(2-thienylpyrrole) derivatives, was performed in close analogy to the electrochemical polymerization methods taught in the prior art.

More particularly, to electropolymerize 3-N-trifluoroacetamidomethyl-2,5-dithienylpyrrole (XIX), a 30 mL solution that is $5.0 \times 10^{-3}$M in the monomer (XIX) and 0.01M in tetraethylammonium tetrachlororuthenate $(C_2H_5)_4NRuCl_4$ in acetonitrile $(CH_3CN)$ is prepared.

In addition, gold anodes were prepared sputtering approximately 1000 Å (Angstroms) of gold onto an appropriate substrate. Suitable substrates include teflon, chrome-treated glass, glass or polystyrene, with the substrate choice depending upon subsequent processing of the conducting film. A prescribed polymer growth area on the anode is defined by screening a 2.25 cm$^2$ pattern. A single cell electrochemical apparatus, consisting of the above-defined anode, a reference electrode of Ag/Ag$^+$ in CH$_3$CN, and a cathode, generally either a platinized titanium mesh or gold sputtered onto abraded glass is used. The cathode has a surface area of approximately 6.5 cm$^2$. The anode and cathode are positioned in parallel and separated by a distance of 2 cm. Prior to polymer synthesis, the electrochemical cell is purged of air by bubbling argon through the solution. A blanket of argon is maintained over the solution during polymer growth.

The observed current varies slightly depending upon the particular 2,5-di(2-thienyl)pyrrole monomer being polymerized. The variance in current is more pronounced if the reaction conditions are altered. However, under the reaction conditions of this general example, a current of approximately 300–400 uA cm$^2$ (microamperes per cm$^2$) is typical. For most applications, 0.2930 Coul cm$^2$ (coulombs cm$^2$) of current are allowed to pass before polymerization is halted. This amount of current corresponds to a conducting polymer thickness of approximately 7325 Å. After electrochemical growth, the conducting polymer films are rinsed thoroughly in sequential acetonitrile baths, and then dried either under vacuum or under an inert argon gas stream.

Bulk conductivity measurements on the polymer film were made after stripping the film from the gold anode by using an epoxy support. To remove the film from the anode, a 0.1 mL aliquot of Master Bond UV14 ultraviolet curable epoxy is applied to the outer surface of the polymer and cured for approximately 2 minutes under a Xenon (Xe) UV lamp. The epoxy-supported film then is etched from the gold surface using GOLD ETCHANT, TYPE TFA, a commercial product available from the Transene Company, Inc.

The conducting polymer films then are thoroughly washed either in water or in water followed by acetonitrile. The conductivity of the polymer film is measured using a four-point probe (Alessi Industries) at a constant current of 15.0 uA (microamperes). However, for polymer films having conductivities less than $1 \times 10^{-2}$ S/cm, it may be necessary to use less current, such as from about 5 to about 10 uA.

Similarly, conducting polymer films were grown on two electrode microdevices by an essentially identical method to the method described above except for the following modifications. The electrode, having a total exposed surface area of approximately 2.7 mm$^2$, is linked in series with a scavenger electrode in order to retain a constant anode area of 2.25 cm$^2$. In addition, the films were grown to thickness of only about 0.07 Coul/cm$^2$ to enhance sensitivity to surface effects.

In accordance with an important feature of the present invention, the conductivity of polymers synthesized from the derivatives of 2,5-di(2-thienyl)pyrrole can be enhanced by copolymerization of the 2,5-di(2-thienyl)pyrrole derivative with pyrrole or other unsubstituted parent heteroaromatic monomers. For example, conducting polymer films were grown from an electrolytic solution containing both pyrrole and a derivatized monomer of structure (XIX). Although it is known that the monomer units comprising the polymer film do not identically reflect the ratio of monomers in the electrolytic solution, it has been proven by infrared, ESCA, conductivity and current versus voltage studies that the derivatized monomer (XIX) was included in the conducting copolymer film.

The initial successful attempt at electrochemical copolymerization utilized a monomer mix of an ethyl ester derivative of pyrrole and pyrrole. As will be detailed more fully hereinafter, a copolymer of the N-trifluoroacetamidomethyl dithienylpyrrole derivative (XIX) and pyrrole introduced a sufficient number of functional sites into the copolymer to allow efficient covalent bonding of an analyte specific probe molecule or a bridging molecule to the polymer. The conductivity of the resulting copolymer films and the number of functional sites present on the copolymer films can be adjusted and regulated by altering the relative concentrations of monomers in solution. As a result, conducting copolymer films possessing conductivities as high as 10 S/cm and having the capability to covalently bind enzymes have been synthesized.

Copolymer films are synthesized in a method analogous to the synthesis of homopolymer films. Generally, the total concentration of oxidizable monomer is maintained at $5.0 \times 10^{-3}$ M. For example, a 1/1 copolymer of pyrrole and 3-trifluoroacetamidomethyl-2,5-dithienylpyrrole (XIX) is grown from a solution that is $2.5 \times 10^{-3}$M in pyrrole and $2.5 \times 10^{-3}$M in monomer (XIX). It has been confirmed using IR, ESCA, current versus voltage experiments and enzyme coupling experiments that both monomers are incorporated into the polymer chain. The ratio of monomer units included in the copolymer chain was not precisely determined, however, the ratio is not equal to the ratio of the monomers in solution.

It was observed that copolymerizing the 3-acetyl derivative of 2,5-di(2-thienyl)pyrrole (XXIV) with pyrrole, under the conditions described above, produced films having a conductivity range ob $2.05 \times 10^{-3}$ to $7.02 \times 10^{-3}$ S/cm, depending upon the monomer ratio.

Normally, a protecting group, such as the trifluoroacetyl group, is placed on the amine group in order to protect the reactive amine moiety during the polymerization process. After polymerization, the trifluoroacetyl group then is removed to allow the amine functionality to react with the bridging molecule or analyte specific probe molecule. However, by varying polymerization conditions, it is possible to directly copolymerize the 3-aminomethyl-2,5-dithienylpyrrole monomer (XVIII), absent the trifluoracetyl protecting group, with pyrrole. In accordance with this direct copolymerization method, the subsequent removal of the blocking group is avoided, and the polymer can be reacted directly with the bridging or specific probe molecule.

In accordance with an important feature of the present invention, the relative amounts of the unsubstituted parent heteroaromatic compound and the 3-substituted 2,5-di(2-thienyl)pyrrole monomer present in the monomer mixture depends upon several variables, including the relative reactivities of the two monomers, the desired conductivity of the conducting copolymer, the number of desired sites in the copolymer for covalently bonding the probe molecule and the general physical and chemical characteristics of the copolymer such as stability, brittleness, solubility, and the like. These variables can be defined by those skilled in the art after considering such factors as the monomers to be used, the analyte to be detected, the polymerization and postpolymerization reaction conditions to be encountered, and the analyte test conditions to be encountered.

In addition to discovering a novel class of monomers, the 2,5-di(2-thienyl)pyrroles (XI) that possess substituents at the three-position of the central ring and can be readily polymerized electrochemically to yield organic conducting polymers, it also has been found that the conducting organic polymers can undergo post-polymerization reactions on the three-position substituents in order to covalently bond bridging molecules or probe molecules to the conducting polymer. By covalently bonding the probe molecule to the conducting polymer either directly or through a bridging molecule, the conducting polymer can be utilized in a diagnostic device as an analyte sensor for the specific analyte that reacts with the probe molecule.

The demonstration that post-polymerization chemistry can be performed on the 3-position substituents of the heteroaromatic ring is an important feature of the present invention. Analogous to the difficulties imposed by steric requirements in growing the conducting polymers, it also can be expected that steric interactions may make the 3-position chemical moiety unavailable for postpolymerization chemistry. In accordance with the present invention, the demonstration that probe molecules can be covalently attached to the chemical moieties on the surface of the conducting polymer is both new and unexpected.

It was demonstrated that the three-position substituent can undergo postpolymerization reaction by the reaction of 3-acetyl-2,5-dithienylpyrrole (XXIV) with phenylhydrazine to yield the corresponding hydrazone derivative. However, in the course of this reaction, the phenylhydrazine also reduced the polymer and therefore destroyed the conductivity of the polymer film.

Another demonstration of postpolymerization polymer surface reactivity was observed in the copolymer films of the 3-trifluoroacetamidomethyl-2,5-dithienylpyrrole (XIX). The copolymer film was produced electrochemically at 0.8 V from a solution that was $2.5 \times 10^{-3}$M in pyrrole, $2.5 \times 10^{-3}$M in the dithienylpyrrole monomer (XIX), and 0.01M in $RuCl_4^-$ counterion. Using a monomer ratio of 9:1 pyrrole/dithienylpyrrole monomer (XIX) produced similar copolymers. After polymerization, the free amine moiety on the polymer surface was exposed by chemically removing the trifluoroacetyl protecting groups, yielding the copolymerized 3-aminomethyl derivative of dithienylpyrrole (XVIII). Among the available methods of removing the trifluoroacetyl blocking group, it was found that exposing the copolymer film to a solution of $1 \times 10^{-2}$M sodium methoxide in methanol ($NaOCH_3/CH_3OH$) for 16 hours at room temperature is preferred. The presence of the free amine moiety on the polymer surface was verified by using radioactive-labeled reactive markers, ESCA studies, and binding studies.

After removal of the trifluoroacetyl protecting group, glucose oxidase was covalently attached to the exposed free amine moieties on the conducting polymer surface by utilizing one of several available chemical reactions. For example, the glucose oxidase was covalently bound to the free amine moieties on the conducting polymer using dimethyl adipimidate dihydrochloride as a bifunctional coupling agent to link the free amine moieties to the lysyl $\epsilon$-amino groups of the glucose oxidase. Successful covalent bonding of the glucose oxidase to the amine moieties was accomplished by exposing the polymer to a solution of 80 mg/mL of dimethyl adipimidate dihydrochloride in 0.25M potassium bicarbonate at pH 10 and 37° C. for ten minutes, followed by minutes exposure to a solution of 0.7 mg/mL glucose oxidase at 37° C. It was found that approximately, $0.5 \times 10^{-12}$ to $1.0 \times 10^{-12}$ moles/cm$^2$ of enzyme was bound to the polymer surface under these conditions. The adipimidate coupling reaction showed that proteins can be covalently attached to the polymer surface. However, other chemical techniques can also be used in order to better retain the electrical properties of the polymer by avoiding the basic conditions required in the adipimidate technique.

For example, an alternate technique for covalently attaching the enzyme to the conducting polymer surface uses monomeric glutaraldehyde as the coupling agent. An effective covalent enzyme coupling has been achieved over a wide range of experimental conditions, therefore demonstrating the flexibility in this technique. Generally, the conditions used to covalently bond the glutaraldehyde to the polymer surface include: activation of the polymer in a solution of 6% glutaraldehyde in 0.1 I phosphate buffer at 37° C. for 24 hours, followed by enzyme coupling in a solution of 0.07 mg/mL glucose oxidase in 0.1 I phosphate buffer at 37° C. for 24 hours.

Analytical investigations have differentiated between glucose oxidase that is non-covalently bound and glucose oxidase that is covalently bound to the polymer film. It has been found that the covalently-bound glucose oxidase is present on the polymer surface at approximately $1 \times 10^{-12}$ to $1.5 \times 10^{-12}$ moles cm$^2$, a value that is consistent with the theoretical value calculated for a monolayer of covalently attached enzyme. The method and conditions utilized in the enzyme attachment procedure are more fully described in the following Example 16.

EXAMPLE XV

Glucose Oxidase Attachment to a Conducting Polymer

The covalent attachment of a biological probe to a conducting polymer surface has been demonstrated by covalently bonding glucose oxidase to the surface of a conducting copolymer film synthesized from pyrrole and 3-trifluoroacetamidomethyl-2,5-dithienylpyrrole (XIX). Similar results were obtained using copolymers obtained from monomer mixtures containing 1/1 and 9/1 ratios of monomers (pyrrole/dithienylpyrrole (XIX)).

After copolymer synthesis, the copolymer film was divided in half. One half of the film was coupled with the enzyme and the other half served as a control. Both halves of the copolymer film were exposed to a solution of $1.0 \times 10^{-2}$M sodium methoxide ($NaOCH_3$) in methanol at room temperature for approximately 16 hours to remove the trifluoroacetyl blocking group and expose the free amine moieties on the copolymer surface. The two films then were washed twice with methanol and twice with 0.1 ionic strength phosphate buffer of pH 7.

It is preferred that glutaraldehyde, the bridging molecule used to couple the copolymer surface amine moieties to the $\epsilon$-amino groups of lysine residues in the enzyme, is monomeric. The presence of monomeric glutaraldehyde can be easily monitored by using UV spectroscopy because polymeric glutaraldehyde exhibits an intense peak at approximately 235 nm (nanometers).

The preferred activation conditions include exposure of the copolymer films to a solution of 6% glutaraldehyde in phosphate buffer at 37° C. for 24 hours. The control half of the film is exposed only to the phosphate buffer and not the glutaraldehyde. Both films then were washed twice with phosphate buffer. The preferred conditions for attachment of the glucose oxidase include exposure of the polymer film, activated with glutaraldehyde, to a solution containing 0.07 mg/mL of the enzyme in phosphate buffer at 37° C. for 24 hours. Both the glutaraldehyde treated half of the polymer film and the control half of the polymer film are exposed to the enzyme solution. Both exposed films then are washed thoroughly in phosphate buffer followed by repeated, agitated washes over the course of several hours in 0.2M Tris buffer (0.25M NaCl) at pH 8 containing 100 microliters of TRITON X-100 surfactant, available from Rohm and Haas Corp., Philadelphia, Pa., per 100 milliliters of buffer.

The amount of enzyme covalently bound to the polymer surface is assayed using a Trinder reaction; wherein 28.5 mL of 2 mM 3,5-dichloro-2-hydroxybenzenesulfonic acid disodium salt, 20 ug/mL horseradish peroxidase, and 0.12M glucose in phosphate buffer is mixed with 150 uL of 4 mM aminoantipyrene. The reaction of glucose oxidase with glucose is kinetically monitored by assaying the resulting dye at 520 nm. A series of solution phase standards was prepared simultaneously in order to quantify the enzyme attachment and to avoid a potential bias that may arise if the activity of the bound enzyme is significantly different than that of the solution phase enzyme.

Utilizing this enzyme attachment technique, enzymes have been covalently bound to a number of polymer films under a wide range of conditions. Typically, using the coupling conditions described above on a 9/1 copolymer film, the glutaraldehyde-treated half of the copolymer film bound $0.99 \pm 0.31$ pmol/cm$^2$ (picomoles/cm$^2$) of enzyme, whereas the control half of the copolymer film bound $0.65 \pm 0.13$ pmol/cm$^2$ of enzyme. The 3/2 ratio in the amount of enzyme coupled to the treated and untreated halves of the copolymer film did not conclusively prove that the enzyme was covalently bound to the copolymer film. However, extensive analytical studies showed that the 3/2 ratio actually does reflect the covalent bonding of the enzyme to the glutaraldehyde. The analytical studies included aging properties, pH optimizing studies and pH stability studies.

The pH stability studies provided most convincing proof of covalent enzyme attachment to the bridging molecule. For example, a pH 10 (0.25M $KHCO_3$) wash of the copolymer films at 37° C. for 24 hours significantly decreased the activity of the non-covalently attached enzyme on the control portion of the film, but only slightly affected the activity of the covalently-bound enzyme on the glutaraldehyde treated portion of the film. Furthermore, the available evidence indicated that this observed effect is due to washing, and not due to denaturing the enzyme. Similarly, discrimination ratios between glutaraldehyde-treated and control films are commonly as high as 20 to 30/1 for films that have been washed in pH 10 potassium bicarbonate solution.

Although the previous example demonstrates the covalent bonding of an enzyme, glucose oxidase, to a bridging molecule, glutaraldehyde, that is in turn bonded covalently to a free amine moiety on the polymer surface, it is not necessary that the moiety on the polymer surface be limited to the amine group. Similarly, the bridging molecule can be any molecule capable of covalently bonding both to the reactive moiety on the polymer surface and to the analyte probe molecule. In addition, if possible, the probe molecule can be bound directly to the surface of the polymer without utilizing a bridging molecule.

For example, depending upon the particular bridging molecule or the particular probe molecule to be bound to the polymer surface, it may be more advantageous to have a moiety other than a free aminomethyl group present on the surface of the molecule. For instance, should a sulfide linkage be desired, a thiol moiety may be introduced on the surface of the conducting polymer. Similarly, in addition to a free nitrogen or sulfur containing moiety on the polymer surface, other useful moieties include those having an oxygen, such as hydroxyl groups; substituted alkyl, such as halogen substituted alkyls; phosphorous containing groups, such as phosphate; and other such moieties having reactive centers, like carbonyl-containing groups or leaving groups, that can react, covalently, with the bridging or probe molecule by addition or substitution reaction mechanisms.

Similarly, the bridging molecules can be any molecule that can covalently bond both to the reactive moiety on the polymer surface and to the probe molecule. The size and chemical structure of the bridging molecule determines the rigidity or flexibility of the link between the probe molecule and conducting polymer, and determines the distance the probe molecule is positioned from the conducting polymer. The flexibility of the bridging arm, and the distance between the probe molecule and conducting polymer surface, can have an effect on the ability of the conducting polymer to sense the analyte in solution. For example, other representative bridging molecules, in addition to glutaraldehyde, include dialdehydes, such as glyoxal, malondialdehyde, succinaldehyde, and adipinaldehyde; and diamines, such as 1,8-octanediamine, 4-aminomethyl-1,8-octanediamine and hexamethylene diamine. In addition to these examples, several other homo-and heterobifunctional spacer arms for the attachment of antibodies, proteins and specific binding sites to the 3-aminomethyldithienylpyrrole (XVIII) are known and are commercially available. These spacer arms are described in the following publications:

Peters, K. and Richards, F. M. (1977) *Ann. Rev. Biochem.* 46, 523-551;

Freedman, R. B. (1979) *Trends in Biochemical Sciences*, September, 193-197;

Das, M. and Fox, C. F. (1979) *Ann. Rev. Biophys. Bioeng.* 8, 165-193;

Ji, T. H. (1979) *Biochim. Biophys. Acta* 559, 39-69; and

Conn. M. (1983) in *Methods in Enzymology* 103, 49-58.

The majority of these bifunctional spacer arms react first with the amino group of the dithienylpyrrole (XVIII), and then can be selectively activated or can react with the amino, sulfhydryl, or other reactive group of the antibody, protein or other probe molecule.

In addition, if permitted by steric interactions and it is so desired, the probe molecule can be covalently bound directly to the conducting polymer surface. Similarly, the bridging molecule can be incorporated into the monomer, as exemplified in monomers XXVI and XXVII. In any event, the presence or absence, type, and size of the bridging molecule will depend upon the nature of the reactive moiety present on the polymer, the nature of the available reactive site on the probe molecule, steric interactions involving the polymer, probe molecule and bridging molecule, and the desired chemical and physical properties of the overall analyte sensing system.

In addition to a novel class of substituted monomers that yield conducting polymers capable of postpolymerization covalent attachment of analyte specific probe molecules, and in accordance with another important feature of the present invention, the presence and concentration of the specific analyte capable of reacting with the probe molecule can be determined. The presence of the analyte and/or its concentration in liquid media can be directly determined because the conductivity of the conducting polymer is altered by the interaction of the probe molecule with the analyte. This measurable electrical effect is detected either through a direct coupling of vibrational interactions arising from the probe molecule-analyte reaction to the conductivity of the polymer or through conductivity changes resulting from secondary effects produced by probe molecule-analyte reaction products.

For the analyte to be detected through a direct coupling of the vibrational energy of the probe/analyte interaction to the phononassisted bipolaron transport of the polymer, the probe molecule must be covalently bound to the conducting polymer surface. As previously defined and as used throughout the specification, a phonon is defined as a quantized, delocalized vibrational or elastic state of the lattice. It is theorized that phonons in conducting polymers are far more localized and molecular in nature than phonons in metals. However, a phonon in conducting polymers is nevertheless delocalized over several monomer units.

As also discussed previously, a bipolaron is the charge carrier in heteroaromatic polymers. A bipolaron is a double charged, localized defect that confines a region of conducting polymer having a stabilized quinoid-like character. The bipolaron is formed through the interaction of two polarons. A bipolaron is illustrated schematically for a generic heteroaromatic polymer in structure (III). Analytical evidence suggests that the bipolaron defect in structure (III) extends over about four to about six monomer units.

In addition, the direct covalent bonding of the probe molecule to the polymer facilitates the electrical detection of the change in polymer conductivity that involve the chemical effects of a secondary species generated by the analyteprobe molecule interaction upon the polymer. The covalent bond between the conducting polymer and the probe molecule increases efficiency by providing a high surface concentration of the secondary reaction product.

As previously discussed, the general class of probe molecules includes proteins that are receptors. Examples of probe molecules include enzymes, antigens, and ion-specific binding sites, like crown ethers. However, other probe molecules can be utilized in the method of the present invention to detect antigens, antibodies, haptens, enzymes, enzyme substrates, enzyme substrate analogs, agglutinins, lectin, enzyme cofactors, enzyme inhibitors, hormones, and like analytes in liquid media. For each analyte, the analyte detection mechanism via the conducting polymer includes a direct observation of an enzyme/substrate or antigen/antibody reaction through the vibrational energy generated from these reactions.

For example, the vibrational excitations induced in the probe molecule by a probe molecule/analyte reaction can be transported through the probe molecule in a localized waveform termed a soliton. This localized energy then can be transmitted to the phonon modes of the conducting polymer by proper selection of the length and stiffness of the molecular coupling arm, i.e., the bridging molecule, between the probe molecule and the polymer. Since the electrical properties of doped heteroaromatic conducting polymers depend upon the excitations of the internal vibrational states of the probe molecule/analyte reactions, the conductivity of the polymer can thereby be directly modulated.

The prior art references regarding the transport of vibrational energy in proteins do not suggest using vibrational energy transport processes as a method of detecting presence and/or concentration of a specific analyte. To date, the principal applications of vibrational energy transport have been in the development of models for the action of muscles.

Therefore, in accordance with the method of the present invention, the reaction between the probe molecule, such as an enzyme, and the analyte produces vibrational interactions that pass through the probe molecule, and the bridging molecule if present, in a stable, pulse-like excitation known as a soliton. In accordance with an important feature of the present invention, the energy of the vibrational interaction can pass as a soliton through the probe molecule and bridging molecule to the conducting polymer. Therefore, it is the efficient transmission of the vibrational energy to the polymer that affects its phonon-assisted bipolaron and produces a change in polymer conductivity. The conductivity change of the polymer then is related to the amount of analyte in solution.

It is an important feature of the present invention that if the soliton mechanism cannot function, the vibrational energy arising from the probe molecule/analyte reaction would be dissipated before reaching the conducting polymer, and therefore preclude analyte concentration determinations. Solitons result from a nonlinear coupling between the vibrational excitation caused by an enzyme/substrate reaction and the resulting deformation in the protein structure caused by the generation of the vibrational excitation.

Soliton transport has been proposed as the mechanism for the useful transport of the energy released during adenosine triphosphate (ATP) hydrolysis. A soliton avoids the thermal dispersion of most localized vibrations by coupling the local vibrations to elastic waves of the host polymers. As a result, a localized energy pulse can be transported over long distances. It is essential that the coupling of this traveling pulse to the polymer phonon modes be effected by a covalent link, otherwise, reflection of the soliton, and dispersion mediated by intervening solvent, severely diminishes the signal.

Solitons are launched only by chemical reactions, and not by the action of heat or light. In addition, solitons will form only under a strong coupling of the internal vibrations of the molecule with a local deformation of the molecule. Therefore, in order to transport the vibrational energy induced by the chemical reaction via a soliton, the molecule must be sufficiently flexible such that it will deform. This deformation can occur in soft chains, like proteins, and serves to transfer energy between different portions of the molecule. In general, a soliton is analogous to a tsunami, or a wave of water that covers extremely long distances without dissipation. The movement of electrons through a superconducting metal is another analogous transmission. Therefore, although a soliton is a wave, its stability allows a soliton to be regarded as particle-like.

In accordance with the method of the present invention, the vibrational excitation caused by the probe molecule/analyte reaction and the resulting molecular deformations balance each other, whereby the vibrational excitation moves through the protein uninhibited. For example, the alpha-helix structure, common in proteins, has the necessary three-dimensional structure that allows a vibrational excitation at one end of the molecule to be transported to the other end of the molecule via a soliton. The alpha-helical proteins possess the correct chemical makeup and stereochemistry to self focus, or trap, the vibrational energy in the stable, pulse-like solitons, to yield an efficient and focused transport of energy.

Therefore, in accordance with the method of the present invention, the vibrational energy created by the reaction between the probe molecule, like a protein, and the analyte will pass to the bridging molecule. Additionally, by the proper selection of the bridging molecule, such that it essentially matches the flexibility, helical structure, hydrogen bonding and/or other chemical and physical characteristics of the probe molecule, the vibrational energy can pass through the bridging molecule reach the conducting polymer to measurably alter the conductivity of the polymer.

In order to generate a soliton, it is essential that the molecule is not too rigid, that the molecule possesses a significant vibrational dipole, and that the molecule possesses sufficient mass. The solitons launched due to the vibrational energy induced in the peptide group by a chemical reaction, can transfer energy along the alpha-helical protein molecule without transformation of the energy into disordered heat motion.

An example of transmitting vibrational energy through a molecule such that observable effects are seen in an area of the molecule relatively far from the reaction site is described by J. Schlessinger et al in *Proc. Nat. Acad. Sci. USA,* 72, 2, 2775-2779 (1975). The authors investigated antibody molecules, known to have a relatively large central fragment, termed $F_c$, and outer fragments, termed $F_{ab}$. Each of these fragments is a protein, with the $F_{ab}$ fragment bonded to the $F_c$ fragment by a disulfide (—S—S—) linkage. The investigators found that the vibrational energy, resulting from a reaction of an antigen with the $F_{ab}$ fragment, can pass undiminished through the $F_{ab}$ fragment and the disulfide linkage to cause a conformation change in the distant $F_c$ fragment. It was also found that if the flexible disulfide linkage was replaced with a rigid linkage, the vibrational energy could not be transported into the $F_c$ antibody fragment. This energy transfer mechanism is analogous to the method of the present invention, wherein the probe molecule and bridging molecule are designed to act as the $F_{ab}$ and disulfide linkage in the antibody and deliver the vibrational energy to the conducting polymer.

The effective transport of vibrational energy in an antibody can be interpreted in a fashion that is distinct but complementary to the soliton description. Following the arguments of Chou in *Biopolymers,* 26:285 (1981), the transport from the $F_{ab}$ portion of the antibody to the $F_c$ portion of the antibody may reflect a resonance interaction involving low frequency vibrations that incorporate large fractions of the molecule. The requirements for transport of such energy are fundamentally the same as those involved in coupling a soliton to the polymer. The invention described herein would also serve to couple resonant, low frequency vibrations to the polymer phonon modes.

Therefore, it is possible to detect the presence and concentration of a specific analyte in solution by measuring the conductivity change in the conducting polymer resulting from the vibrational energy of the probe molecule-analyte reaction and transported by a soliton. For example, the $F_{ab}$ fragment of an antibody can be covalently bound, through a disulfide linkage or a helical structure, to a conducting polymer. The subsequent reaction between a specific antigen and the $F_{ab}$ fragment of the antibody launches a soliton to transport the vibrational energy of the reaction to the conducting polymer. The transferred vibrational energy alters the conductivity of the conducting polymer and therefore allows detection and measurement of the antigen. Furthermore, it is not essential that all of the vibrational energy be transported to the conducting polymer because it has been calculated that a loss of 70% of the vibrational energy nevertheless generates a 10% change in conductivity.

The antigen detection mechanism of the present invention is especially useful because direct monitoring of antibody-antigen reactions by the prior art methods has proven very inefficient. Therefore, in accordance with an important feature of the present invention, the antibody-antigen reaction can be detected and monitored via on-off fluctuation spectroscopy. This particular technique can measure the noise generated by the antigen-antibody reaction. Each antigen-antibody reaction creates a vibrational energy pulse that travels through the probe molecule via a soliton to cause a temporary change in the conductivity of the polymer. By measuring this noise, i.e., the change in conductivity of the conducting polymer, and by determining the number of conductivity spikes generated, the presence and amount of a specific antigen can be determined.

In accordance with another important feature of the present invention, the transducing of the probe molecule/analyte interaction into an electrical signal within the conducting polymer also can be accomplished, or enhanced, by a secondary process. For instance, ammonia affects the conductivity of polypyrrole, therefore permitting the detection of ammonia because as ammonia concentration increases, polypyrrole conductivity decreases. In the method of the present invention, the detection of a reaction product of an enzyme-substrate reaction can be accomplished either through direct compensation of the dopant counterion or more reversibly by selecting a counterion polymer dopant that also serves as a catalyst for the secondary reaction. For example, tetrachlororuthenate ($RuCl_4^-$) or tetrachloroferrate (III) ($FeCl_4^-$) can act as a dopant-catalyst for the oxidation of hydrogen peroxide. For example, since hydrogen peroxide is generated in the reaction of glucose oxidase with glucose in the presence of oxygen, a method for determining glucose concentrations in solutions is available. Although the use of a dopant-catalyst as an electrical transducer in heteroaromatic polymers is fully taught in U.S. Pat. No. 4,560,534, in accordance with the method of the present invention, the ability to covalently bond the enzyme to the conducting polymer surface significantly enhances the effectiveness of the transduction mechanism by ensuring a high local surface concentration of the peroxide.

In general, it has been found that the method of the present invention can be used to detect the presence and concentration of a specific analyte in liquid media. In addition, the detection data show that the mechanism of analyte detection involves both the primary effect of vibrational coupling between the probe molecule and the polymer and a secondary effect produced by the supporting electrolyte counterion on the reaction product of the probe molecule-analyte reaction.

In particular, a microelectrode device consisting of an interdigited pair of gold electrodes with an insulating spacing of 25 u (microns) served as a template for the analyte sensor. The trifluoroacetamidomethyl derivative of dithienylpyrrole (XIX) and pyrrole were electrochemically polymerized under previously described conditions to yield a conducting copolymer film of approximately 1800 Å thickness. The copolymer bridged the insulating gap, thereby covering the entire device with copolymer film. Although the uniformity of the film thickness was not monitored, it was determined that the copolymer film was thinnest above the insulating regions of the template. After removing the trifluoroacetyl protecting group, glucose oxidase was attached to the conducting copolymer film using the dimethyl adipimidate procedure discussed previously. The microelectrode devices then were mounted in a flow-through cell and exposed to varying concentrations of hydrogen in buffer as well as 1000 mg/dL samples of D- and L-glucose.

An approximately linear dose response to hydrogen peroxide was observed over the concentration range of 0.044–0.88 mM. In addition, a D-glucose response was observed that was approximately comparable to the hydrogen peroxide response at 0.44 mM. Significantly, no response to L-glucose was observed therefore demonstrating that the sensitivity to D-glucose actually was induced enzymatically.

The magnitude of the response also is significant. By assuming a diffusion rate for hydrogen peroxide of approximately $6 \times 10^{-6} cm^2/sec$ and a surface coverage of approximately 0.6 pmol/cm$^2$, it can be shown that a local concentration of 0.4 mM hydrogen peroxide cannot be sustained because the diffusion rate of the hydrogen peroxide from the conducting copolymer film would far exceed the generation rate of hydrogen peroxide. Therefore, the response of the microelectrode device to the glucose involved more than merely the enzymatic production of hydrogen peroxide. As a result, indirect evidence exists for the vibrational coupling mechanism between the enzyme/substrate reaction and the conducting polymer. This analyte detection mechanism is both surprising and unexpected, and is not suggested in the prior art.

In regard to hydrogen peroxide generation, the amount of enzyme covalently bound to the conducting copolymer film is not sufficient to produce and maintain a significant macroscopic hydrogen peroxide coverage on the electrode. As a result, over a small region (like 50 Å), the hydrogen peroxide concentration must decrease from the local surface value to approximately zero. If the local surface value is assumed to be 0.5 mM ($5 \times 10^{-7}$ mol/cm$^3$), then the flux (J) of hydrogen peroxide away from the 50 Å surface region ($J = D\Delta C/L$, wherein J is the flux, D is the diffusion coefficient ($6 \times 10^{-6}$ cm$^2$/sec), C is the concentration drop ($5 \times 10^{-7}$ moles/cm$^3$) and L is the distance over which the concentration drops ($5 \times 10^{-7}$ cm), is approximately $6 \times 10^{-6}$ mol/sec/cm$^2$. The generation rate of hydrogen peroxide is determined by the surface concentration of the enzyme on the conducting copolymer. Assuming an activity of 20 units/mg, a production rate for hydrogen peroxide of $1.192 \times 10^{-12}$ moles/sec/cm$^2$ is calculated. Clearly, the production rate for hydrogen peroxide cannot compete with the diffusion rate, therefore precluding a local hydrogen peroxide concentration of 0.5 mM.

The primary features relating to the method of the present invention have been repeatedly observed. The new and unexpected results arising from the method of the present invention will result in diagnostic devices designed to assay liquid media for specific analytes.

From the foregoing, it is seen that the present invention is well adapted to attain all of the objects hereinabove set forth, together with other advantages that are obvious and are inherent to the analyte detection system. The invention has the advantages of convenience, simplicity, relative economy, positiveness, effectiveness, durability, accuracy and directness of action. Among the advantages of the present invention is that the method operate nonoptically, can be constructed at relatively low cost, have a great degree of flexibility with respect to format, and can be constructed to have a relatively small size.

Although the present invention is primarily directed to assaying liquid media for various clinically significant substances or constituents in biological fluids, such as urine and blood, including lysed or unlysed blood, blood plasma, blood serum, it should be understood that the method of the present invention can be utilized for the detection of nonbiological fluids, including swimming pool water, wines, etc.

It will be understood that the present disclosure has been made only by way of preferred embodiment and that numerous changes in details of construction, combination, and arrangement of parts can be resorted to without departing from the spirit and scope of the invention as hereunder claimed.

We claim:

1. Substituted bithiophenes and dithienylpyrroles characterized by the formulae:

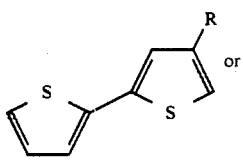  or  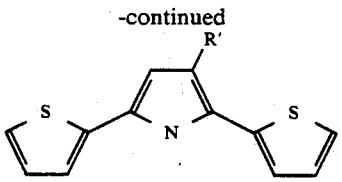

wherein R is N-trifluoroacetamidomethyl, 2-hydroxyethyl, 2-phthalimidoethyl, 2-trifluoroacetamidoethyl, acetyl, carboxyethyl, carboethoxyethyl, carbomethoxyethyl, (N-3-carbomethoxypropionyl)aminoethyl, (N-3-carboxypropionyl)amiomethyl, 2-methyldithioethyl, (N-imidazocarbonyl)amidomethyl, (4-nitrophenylcarbamoyl)amidomethyl, formylmethyl or carboxymethyl and R' is cyano, aminomethyl, N-trifluoroacetamidomethyl, 2-hydroxyethyl, 2-phthalimidoethyl, 2-aminoethyl, 2-trifluoroacetamidoethyl, acetyl, carboxyethyl, carboethoxyethyl, carbomethoxyethyl, (N-3-carbomethoxypropionyl)aminoethyl, (N-3-carboxypropionyl)aminomethyl, 2-methyldithioethyl, (N-imidazocarbonyl)amidomethyl, (4-nitrophenylcarbamoyl)amidomethyl, formylmethyl or carboxymethyl.

2. The bithiophenes and dithienylpyrroles of claim 1 wherein R and R' are 2-trifluoroacetamidoethyl.

3. The dithienylpyrroles of claim 1 wherein R' is cyano, aminomethyl or 2-aminoethyl.

* * * * *